(12) United States Patent
Kurokawa et al.

(10) Patent No.: US 12,272,159 B2
(45) Date of Patent: Apr. 8, 2025

(54) DRIVING ANALYSIS DEVICE AND DRIVING ANALYSIS METHOD FOR ANALYZING DRIVER TENDENCY

(71) Applicant: DENSO CORPORATION, Kariya (JP)

(72) Inventors: Keisuke Kurokawa, Kariya (JP); Kaname Ogawa, Kariya (JP)

(73) Assignee: DENSO CORPORATION, Kariya (JP)

( * ) Notice: Subject to any disclaimer, the term of this patent is extended or adjusted under 35 U.S.C. 154(b) by 371 days.

(21) Appl. No.: 17/826,403

(22) Filed: May 27, 2022

(65) Prior Publication Data

US 2022/0284718 A1    Sep. 8, 2022

Related U.S. Application Data

(63) Continuation of application No. PCT/JP2020/044557, filed on Nov. 30, 2020.

(30) Foreign Application Priority Data

Dec. 2, 2019    (JP) ................................ 2019-218107

(51) Int. Cl.
| | |
|---|---|
| G06V 20/59 | (2022.01) |
| B60K 35/00 | (2006.01) |
| G06T 7/73 | (2017.01) |
| G06T 11/20 | (2006.01) |
| G06V 10/62 | (2022.01) |
| G06V 10/766 | (2022.01) |
| B60K 35/65 | (2024.01) |

(52) U.S. Cl.
CPC ............ *G06V 20/597* (2022.01); *B60K 35/00* (2013.01); *G06T 7/74* (2017.01); *G06T 11/206* (2013.01);

(Continued)

(58) Field of Classification Search
None
See application file for complete search history.

(56) References Cited

U.S. PATENT DOCUMENTS

| | | |
|---|---|---|
| 2003/0181822 A1 | 9/2003 | Victor |
| 2005/0073136 A1 | 4/2005 | Larsson et al. |

FOREIGN PATENT DOCUMENTS

| | | | |
|---|---|---|---|
| CN | 108537161 A | * | 9/2018 |
| JP | H10272960 A | | 10/1998 |

(Continued)

OTHER PUBLICATIONS

English translation of JP-2004192345-A. (Year: 2004).*

(Continued)

*Primary Examiner* — Thomas D Lee
(74) *Attorney, Agent, or Firm* — Harness, Dickey & Pierce, P.L.C.

(57) ABSTRACT

In a driving analysis device, an information generation unit generates a time series of detection elements including a line-of-sight direction indicating to which of a plurality of preset viewable areas a line of sight of a driver driving a vehicle is oriented and an open/closed state of driver's eyes. An acquisition unit acquires evaluation data from the time series of the detection elements using a time window having a preset time width. An extraction unit extracts a plurality of feature quantities including at least a result of summation of appearance frequencies with respect to each of the detection elements from the evaluation data. An analysis unit analyzes a driver's tendency using a function that receives, as input, at least a part of the feature quantities extracted by the extraction unit.

8 Claims, 21 Drawing Sheets

(52) U.S. Cl.
CPC ............ G06V 10/62 (2022.01); G06V 10/766 (2022.01); *B60K 35/65* (2024.01); *B60K 2360/741* (2024.01); *G06T 2207/20081* (2013.01); *G06T 2207/20084* (2013.01); *G06T 2207/30201* (2013.01); *G06T 2207/30268* (2013.01)

(56) References Cited

FOREIGN PATENT DOCUMENTS

| | | | |
|---|---|---|---|
| JP | 2004192345 A | * | 7/2004 |
| JP | 2010131401 A | | 6/2010 |
| JP | 2017211882 A | | 11/2017 |
| JP | 2018075255 A | | 5/2018 |
| JP | 2020126753 A | | 8/2020 |
| WO | WO-2021112038 A1 | | 6/2021 |

OTHER PUBLICATIONS

English translation of CN-108537161-A. (Year: 2018).*
"One Millisecond Face Alignment with an Ensemble of Regression Trees", Vahid Kazemi and Josephine Sullivan, The IEEE Conference on CVPR, 2014.
"Greedy Function Approximation: A gradient boosting machine" Jerome H. Friedman, The Annals of Statistics vol. 29, No. 5 (2001), 1189-1232.

* cited by examiner

FIG. 4
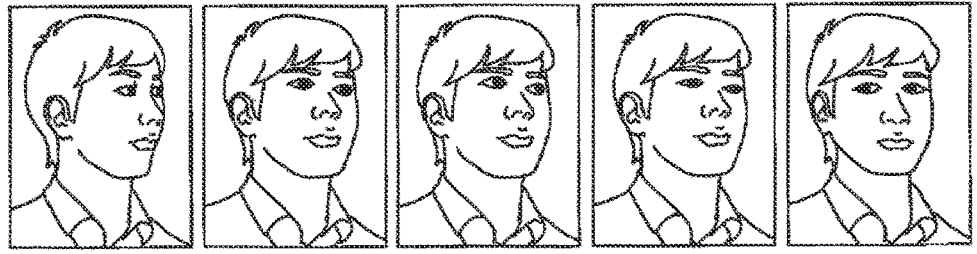
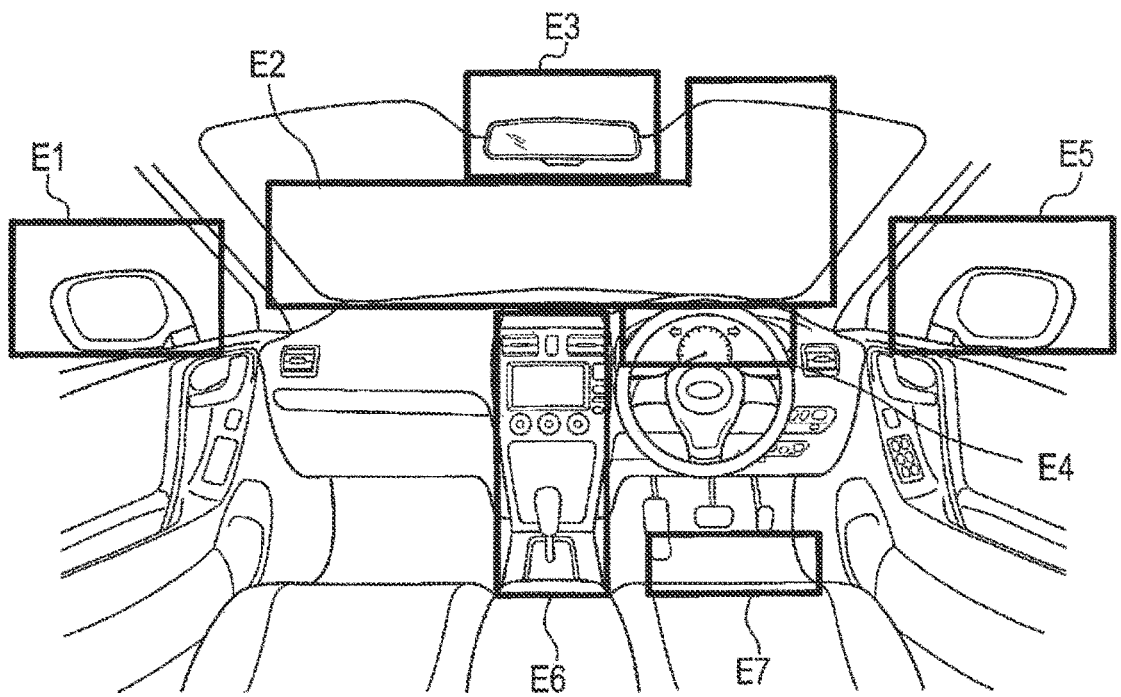
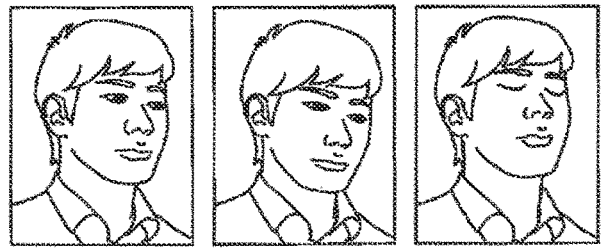

FIG. 15

| CLOSED EYES | LEFT MIRROR | FRONT | REAR MIRROR | METER | RIGHT MIRROR | PERCLOS | CLOSED-EYES TIME | BLINKING CYCLE | CLOSED-EYES FREQUENCY | activity |
|---|---|---|---|---|---|---|---|---|---|---|
| 41 | 69 | 669 | 16 | 3 | 4 | 0.051122 | 2.928571 | 54.35714 | 0.017456 | 0 |
| | 41 | 671 | 17 | 3 | 4 | 0.050369 | 2.928571 | 55.21429 | 0.017199 | 1 |
| | 78 | 665 | 24 | 0 | 4 | 0.036697 | 3.2 | 84 | 0.011468 | 2 |
| 32 | 147 | 867 | 0 | 1 | 0 | 0.021111 | 1.461538 | 67.76923 | 0.014444 | 3 |
| 19 | 13 | 693 | 17 | 0 | 2 | 0.205357 | 20.44445 | 64.72727 | 0.012277 | 2 |
| 184 | 0 | | | | | | | | | |

IDENTICAL UNIT — DIFFERENT UNITS

SUMMARY VALUE OF FREQUENCIES FOR EYE STATES E1 TO E8

FEATURE QUANTITIES BASED ON CLOSED-EYES E8

EXPLANATORY VARIABLE (INPUT INFORMATION GROUP $I_E$)

OBJECTIVE VARIABLE (DRIVER'S CONDITION)

DRIVING ANALYSIS DEVICE AND DRIVING ANALYSIS METHOD FOR ANALYZING DRIVER TENDENCY

CROSS REFERENCE TO RELATED APPLICATIONS

The present application is a continuation application of International Patent Application No. PCT/JP2020/044557 filed on Nov. 30, 2020, which designated the U.S. and claims the benefit of priority from Japanese Patent Application No. 2019-218107 filed on Dec. 2, 2019. The entire disclosures of all of the above applications are incorporated herein by reference.

TECHNICAL FIELD

The present disclosure relates to a driving analysis device and a driving analysis method for analyzing a driver's condition from an image of the driver.

BACKGROUND

There is a technology of identifying and evaluating the features of deterioration in a driver's health by detecting the orientations of the driver's eyes and head. The features of health deterioration include a driver's perceptive or visual inattentiveness and increase in work load on a driver. Specifically, a percentage of road center (hereafter, abbreviated as PRC), which is a ratio of a gaze at the road front, is calculated from a sum of a time for which a driver looks at the road front that is a direction a driver's eyes are typically oriented during driving and a time for which the driver glances at other directions than the road front. Then, the calculated PRC is used to evaluate inattentiveness, health deterioration, and the like.

SUMMARY

The present disclosure describes a driving analysis device that: generates a time series of detection elements including a line-of-sight direction indicating to which of a plurality of preset viewable areas a line of sight of a driver driving a vehicle is oriented and an open/closed state of driver's eyes; acquires evaluation data from the time series of the detection elements using a time window having a preset time width; extracts a plurality of feature quantities including at least a result of summation of appearance frequencies with respect to each of the detection elements from the evaluation data; and analyzes at least one of a driver's tendency and a driver's condition using a function receiving, as input, at least a part of the feature quantities extracted.

BRIEF DESCRIPTION OF DRAWINGS

Features and advantages of the present disclosure will become more apparent from the following detailed description made with reference to the accompanying drawings, in which:

FIG. 4 is an explanatory diagram showing examples of viewable areas and eye states;

FIG. 15 is an explanatory diagram showing an example of values of feature quantities and limitations related to comparative data generation;

DETAILED DESCRIPTION

To begin with, a relevant technology will be described only for understanding the embodiments of the present disclosure.

As a relevant technology, the PRC is calculated from a sum of a time for which a driver looks at the road front that is a direction a driver's eyes are typically oriented during driving and a time for which the driver glances at other directions than the road front, and the calculated PRC is used to evaluate inattentiveness, health deterioration, and the like. In the relevant technology, as the result of the present inventors' close examination, the following drawbacks have been found. Namely, since the PRC is used for evaluation, even a case where a driver intentionally looks at a direction other than the front may be evaluated as health deterioration, inattentiveness, or the like. Further, any other condition than health deterioration and inattentiveness, a driver's intentional action, or the like may not be precisely evaluated.

According to an aspect of the present disclosure, it is provided a technology of analyzing a driver's various conditions, including the driver's intentional action, from an image of the driver.

According to an aspect of the present disclosure, it is provided a driving analysis device including an information generation unit, an acquisition unit, an extraction unit, and an analysis unit.

The information generation unit generates a time series of detection elements including a line-of-sight direction indicating to which of a plurality of preset viewable areas a line of sight of a driver driving a vehicle is oriented and an open/closed state of driver's eyes. The acquisition unit acquires evaluation data from the time series of the detection elements by using a time window having a preset time width. The extraction unit extracts, from the evaluation data, a plurality of feature quantities including at least a result of summation of an appearance frequency with respect to each of the detection elements. The analysis unit analyzes at least one of a driver's tendency and a driver's condition by using a function taking, as an input, at least a part of the feature quantities extracted by the extraction unit.

According to such a configuration, unlike the relevant technology, an analysis is made without paying special attention to the front direction. Therefore, a state in which a driver is intentionally viewing any other direction than the front direction can be precisely determined and misidentification as inattentiveness or the like can be suppressed.

In addition to information about a gazing direction, information about a closed-eye state is also used for analyses. Therefore, the accuracy of analysis of a driver's condition, such as health deterioration and inattentiveness, can be enhanced.

Hereafter, a description will be given to embodiments of the present disclosure with reference to the drawings.

<1. First Embodiment>
<1.1. Configuration>

Figure 1:
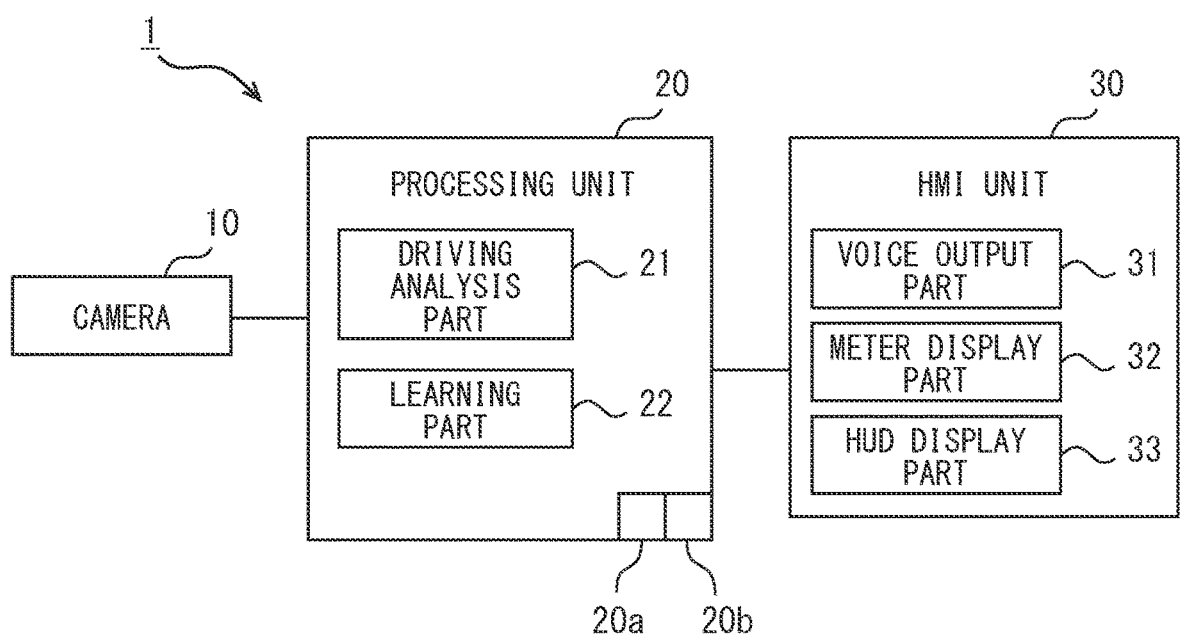
FIG. 1 is a block diagram illustrating a configuration of a driving analysis device.

The driving analysis device 1 shown in FIG. 1 is mounted in a vehicle and analyzes a driver's condition or the like by analyzing the driver's face orientation, line-of-sight direction, or the like. The driver's condition to be analyzed may include sound, drowsy, and desultory driving.

The driving analysis device 1 includes a camera 10 and a processing unit 20. The driving analysis device 1 may include an HMI unit 30. The processing unit 20, the camera 10, and the HMI unit 30 may be directly connected with one another or may be connected with one another via such an in-vehicle network as CAN. The CAN is a registered trademark and the abbreviation of Controller Area Network.

For the camera 10, for example, a publicly known CCD image sensor, CMOS image sensor, or the like can be used. The camera 10 is disposed, for example, so that the face of a driver sitting on the driver's seat of the vehicle is embraced in an imaging range. The camera 10 periodically picks up an image and outputs data of a picked-up image to the processing unit 20.

The processing unit 20 includes a microcomputer having CPU 20a and such semiconductor memory (hereafter, referred to as memory 20b) as RAM or ROM. The processing unit 20 includes a driving analysis part 21 and a learning part 22 as blocks representing functions implemented by the CPU 20a executing a program. The details of processing by the driving analysis part 21 and the learning part 22 will be described later.

The HMI unit 30 includes a voice output part 31, a meter display part 32, and an HUD display part 33. The HMI is the abbreviation of human machine interface.

The voice output part 31 is a device generating a warning sound or voice via a speaker equipped in the vehicle.

The meter display part 32 is a device for displaying results of measurement of vehicle speed, a number of engine revolutions, remaining fuel quantity, and the like measured in the vehicle. The HUD display part 33 is a device showing varied information by projecting an image onto a wind shield or a combiner. The HUD is the abbreviation of head up display. An area for presenting a result of analysis by the driving analysis part 21 is provided in a display screen of at least one of the meter display part 32 and the HUD display part 33.

<1.2. Driving Analysis Processing>

Figure 2:
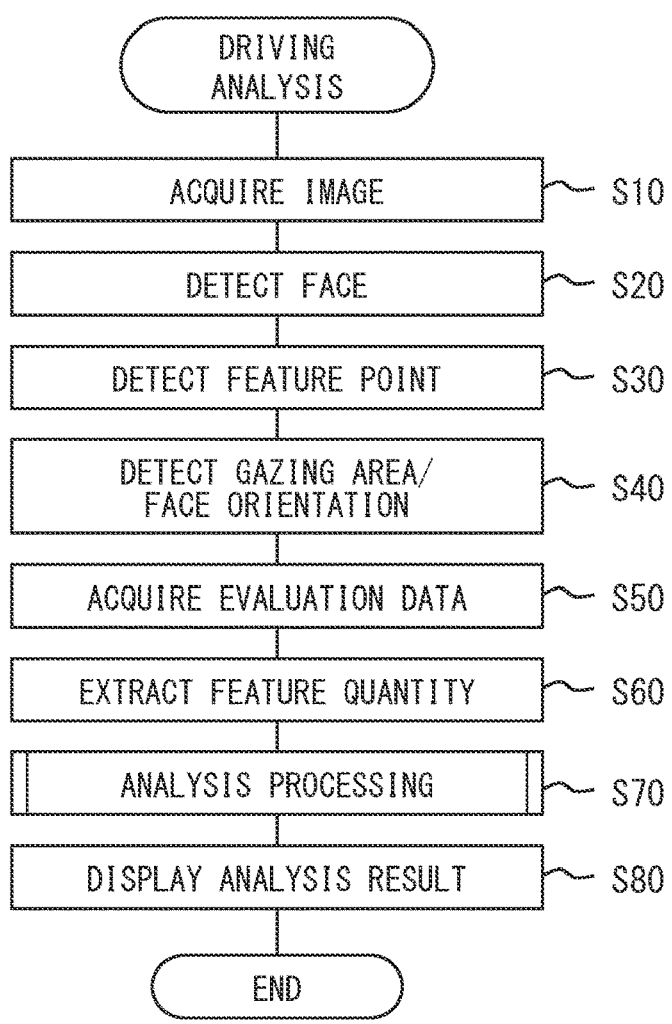
FIG. 2 is a flowchart of driving analysis processing.

A description will be given to driving analysis processing performed by the processing unit 20 to implement the functions of the driving analysis part 21 with reference to the flowchart in FIG. 2. The driving analysis processing is repeatedly launched in a preset cycle (for example, ½0 to ⅓0 seconds).

At S10, the processing unit 20 acquires an image equivalent to one frame from the camera 10.

Figure 3:
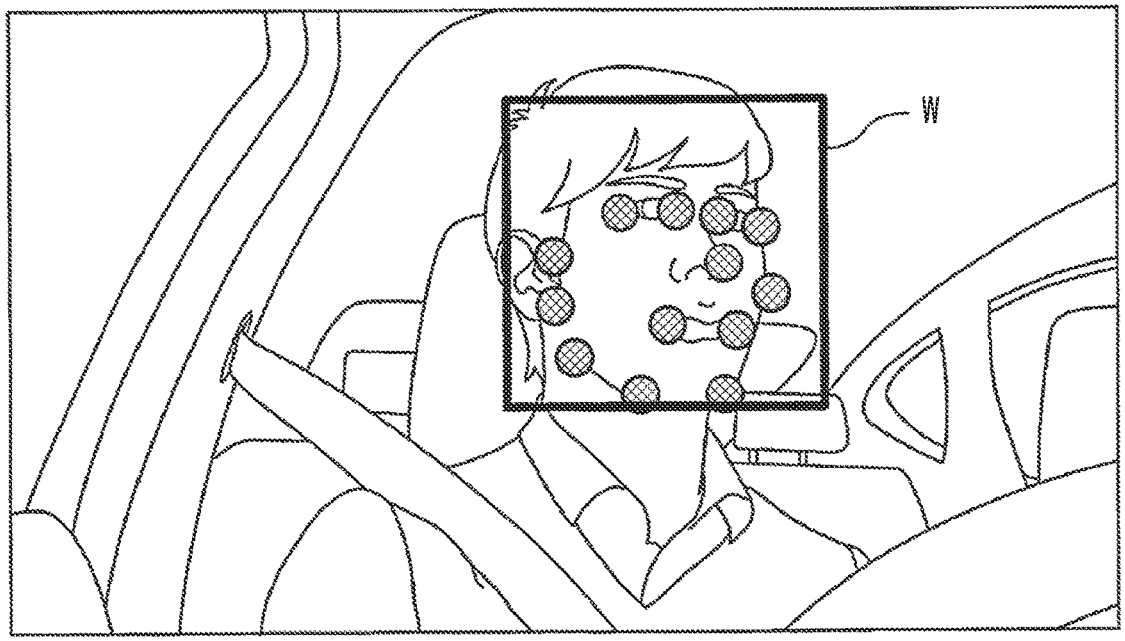
FIG. 3 is an explanatory diagram showing an acquired image and results of face detection and face feature point detection.

At S20, subsequently, the processing unit 20 performs face detection processing. The face detection processing is processing to detect a face area, which is an area where an image of a face is picked up, from the image acquired at S10. In the face detection processing, for example, pattern matching can be used but the present disclosure is not limited to pattern matching. As the result of the face detection processing, for example, the portion indicated by the frame W in FIG. 3 is detected as a face area.

At S30, subsequently, the processing unit 20 performs feature point detection processing. The feature point detection processing is processing to use an image of the face area extracted at S20 to detect a plurality of face feature points required for identifying the orientation of the imaged face and the state of the eyes thereof. For the face feature points, characteristic parts of contours of such as eyes, nose, mouth, ears, and face are used. As the result of the feature point detection processing, for example, a plurality of face feature points indicated by the meshed circles in FIG. 3 are detected.

At S40, subsequently, the processing unit 20 performs gazing area/face orientation detection processing. The gazing area/face orientation detection processing is processing in which an image in the vicinity of the eyes detected from an image of the face area based on the face feature points detected at S30 is used to detect a direction at which the driver gazes, the open/closed state of the driver's eyes, and the driver's face orientation and a result of the detection is accumulated in the memory 20b. In the memory 20b, at least detection results equivalent to a number of frames corresponding to the maximum width of a time window described later are accumulated.

A driver's gazing direction is represented by dividing a range viewed by a driver during driving into a plurality of areas (hereafter, referred to as viewable areas) and identifying at which viewable area the driver is gazing. As shown in FIG. 4, the viewable areas include a left side mirror (hereafter, referred to as left mirror) E1, the front E2, an inside rear view mirror (hereafter, referred to as rear mirror) E3, a meter E4, a right side mirror (hereafter, referred to as right mirror) E5, a console E6, and arm's reach E7. However, how to divide a viewable area is not limited to that indicated by E1 to E7 and more finely divided viewable areas may be used or viewable areas divided by an angle or the like as viewed by a driver may be used.

A driver's open/closed state, cited here, indicates whether the driver does not look at any viewable area as the result of his/her eyes being closed. This state is expressed as closed-eyes E8.

Any piece of the status information of the viewable areas E1 to E7 is binarily expressed. When it is determined that the driver is gazing at a relevant viewable area, 1 is set and when it is determined that the driver is not gazing at that viewable area, 0 is set. The status information of closed-eyes E8 is also binarily expressed: when the driver is in a closed-eyes state, 1 is set and when the driver is not in a closed-eyes state, 0 is set.

With respect to the status information of the viewable areas E1 to E7 and the closed-eyes E8, at any time, any one piece of information uniquely takes 1 and all the other pieces of information take 0.

Figure 5:
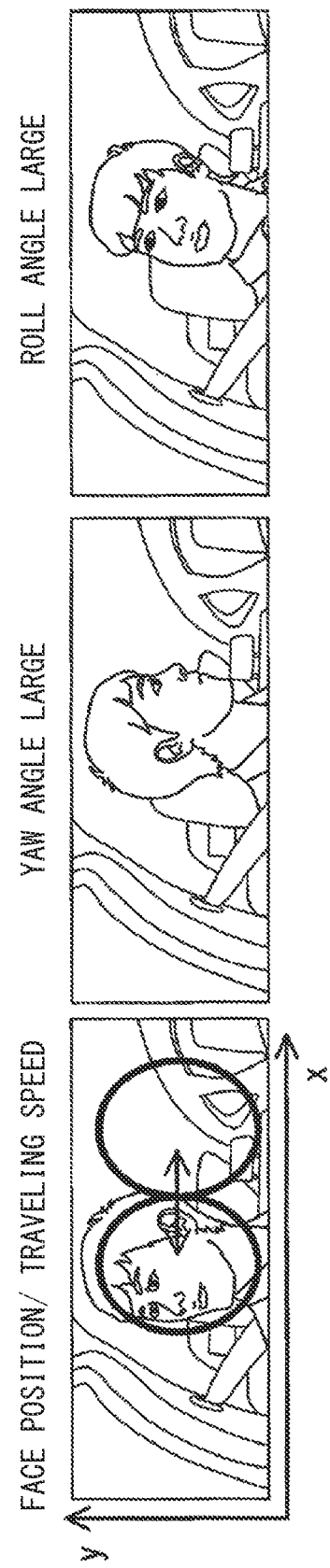
FIG. 5 is an explanatory diagram showing example of face states.

With respect to a driver's face orientation, as partly shown in FIG. 5, to what extent the orientation of the driver's face is rotated or inclined is expressed by angle for each of yaw direction $\theta 1$, pitch direction $\theta 2$, and roll direction $\theta 3$. The yaw direction $\theta 1$ represents an angle in the direction of rotation around a neck. The pitch direction $\theta 2$ represents an inclination angle in the front-back direction of a face. The roll direction $\theta 3$ represents an inclination angle in the lateral direction of a face. Aside from a driver's face orientation, the driver's face position may be detected.

In the following description, the viewable areas E1 to E7 and the closed-eyes E8 will be collectively referred to as eye states E1 to E8 and the yaw direction $\theta 1$, pitch direction $\theta 2$, and roll direction $\theta 3$ representing a driver's face orientation will be collectively referred to as face states $\theta 1$ to $\theta 3$.

In the processing of S30 and S40, for example, a method for detecting a feature point and detecting a gazing direction using a regression function, proposed in JP 2020-126573 A, which is incorporated herein by reference, or the like can be used.

Figure 6:
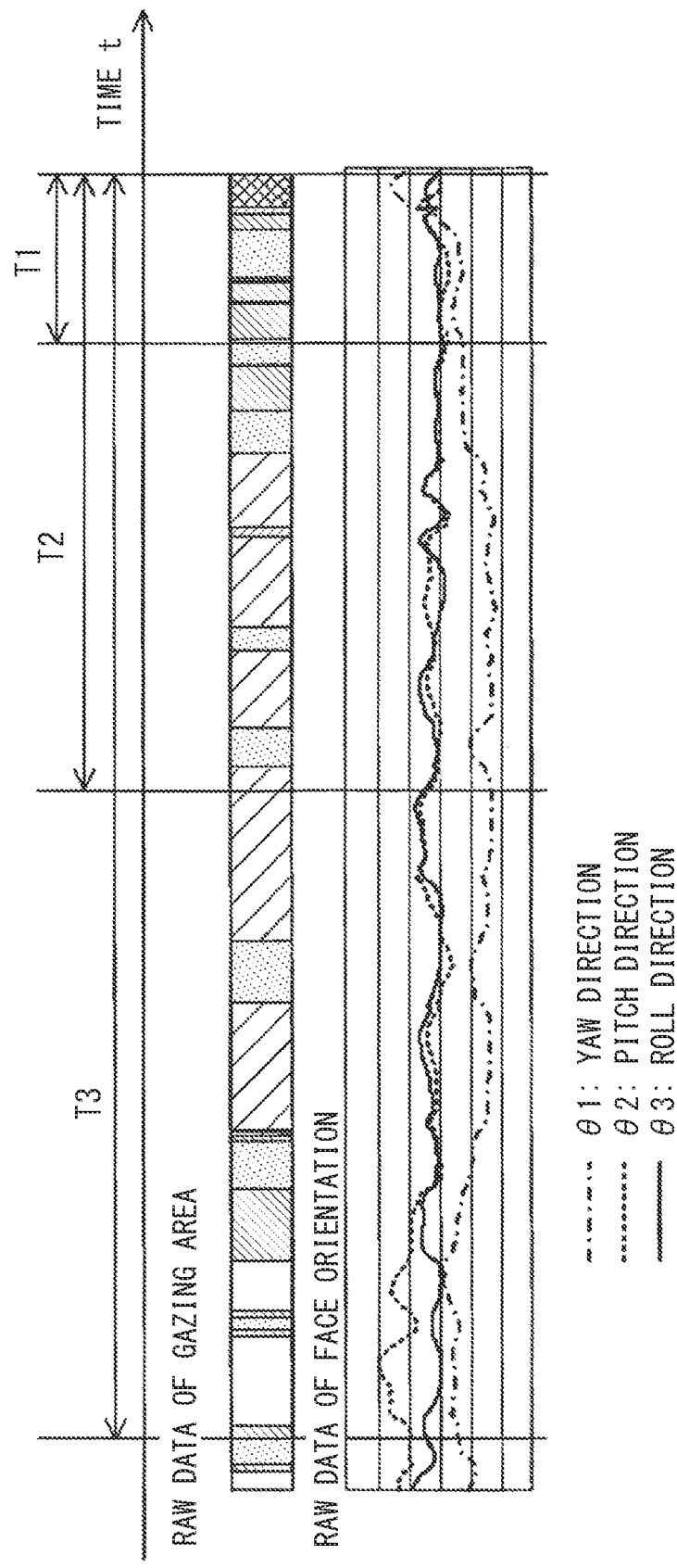
FIG. 6 is an explanatory diagram showing an example of raw data of gazing areas and face orientations and a time window used for evaluation data extraction.

At S50, subsequently, the processing unit 20 uses a time window to extract evaluation data from time series data of the eye states E1 to E8 and face states $\theta 1$ to $\theta 3$ accumulated in the memory 20b. As shown in FIG. 6, a time window is set to a predetermined time width in the past relative to the current time. A time width may be set to different lengths according to an analysis target. For example, to detect front carelessness, a relatively short time width T1 (for example, approximately 3 seconds) is set. To confirm an ambient environment, a longer time width T2 (for example, approximately 15 seconds) is set. To detect drowsiness, a further longer time width T3 (for example, approximately 30 seconds) is set.

The raw data of gazing area shown in FIG. 6 is generated by arranging eye states having a value of 1 among the eye states E1 to E8 along a time base. The time widths T1 to T3 of time windows may be changed according to an application utilizing an analysis result of the relevant driving analysis processing or may be a plurality of different types of time widths T1 to T3 may be simultaneously used. The raw data of face orientation is generated by arranging the angles of face states $\theta 1$ to $\theta 3$ represented relative to a traveling direction of the vehicle along a time base.

At S60, subsequently, the processing unit 20 uses the extracted evaluation data to extract a feature quantity.

A feature quantity may include a result of summing a frequency with which the values of the eye states E1 to E8 take 1 (that is, a number of image frames) with respect to each of the eye states E1 to E8. Further, a feature quantity may include a duration of one eye state, a transition interval, and the like. Furthermore, a feature quantity may include a frequency of transition from a first eye state to a second eye state (for example, front→right mirror, or the like), a transition interval thereof, and the like.

A feature quantity may include a closed-eyes time (hereafter, referred to as PERCLOS) per unit time, a number of times of closed-eyes per unit time (hereafter, referred to as closed-eyes frequency), a closed-eyes cycle, a mean closed-eyes time per time, and the like calculated by paying attention to the closed-eyes E8 in the raw data of gazing area.

Figure 7:
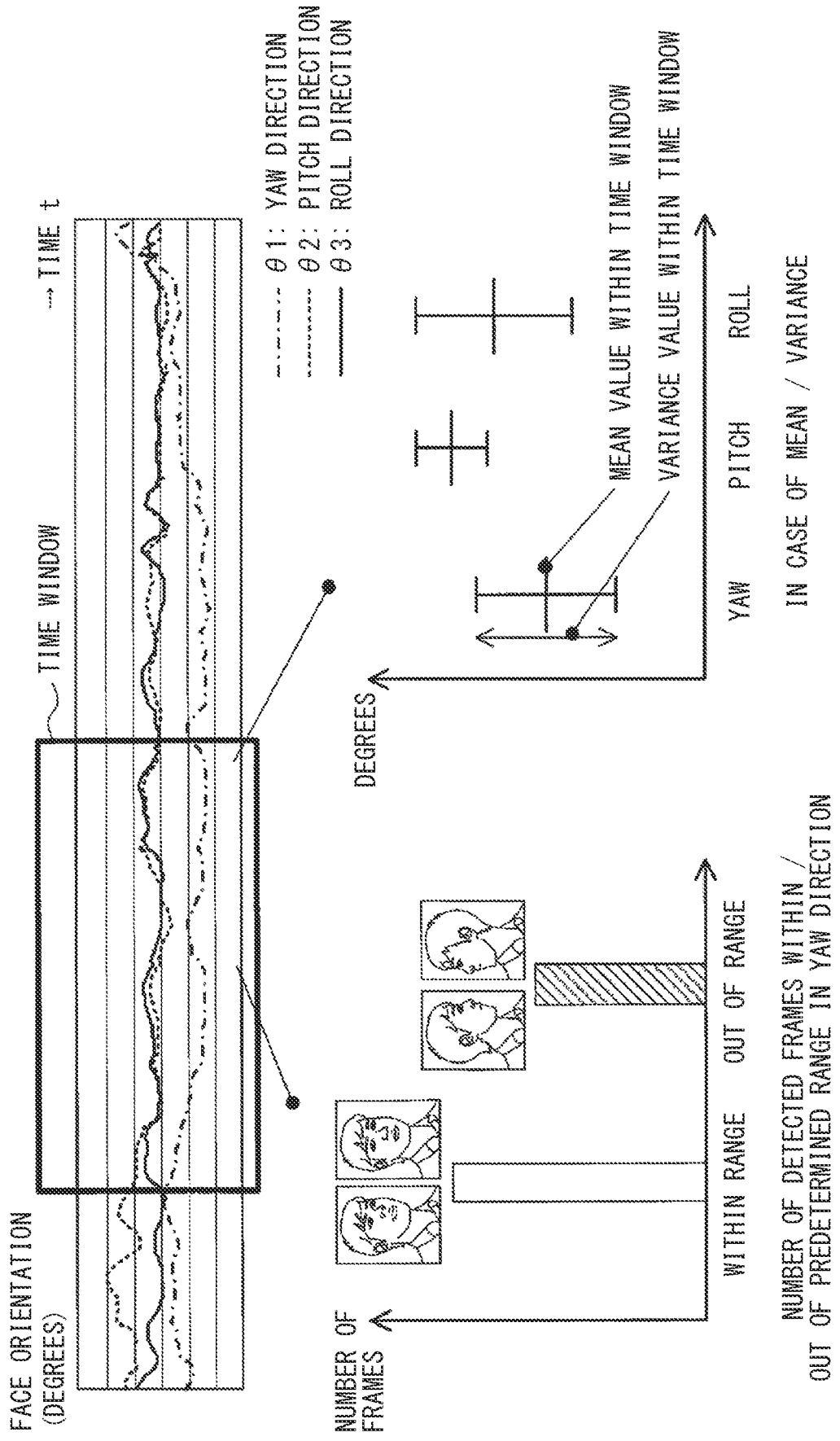
FIG. 7 is an explanatory diagram showing an example of feature quantities generated from the raw data of the face orientations.
Figure 8:
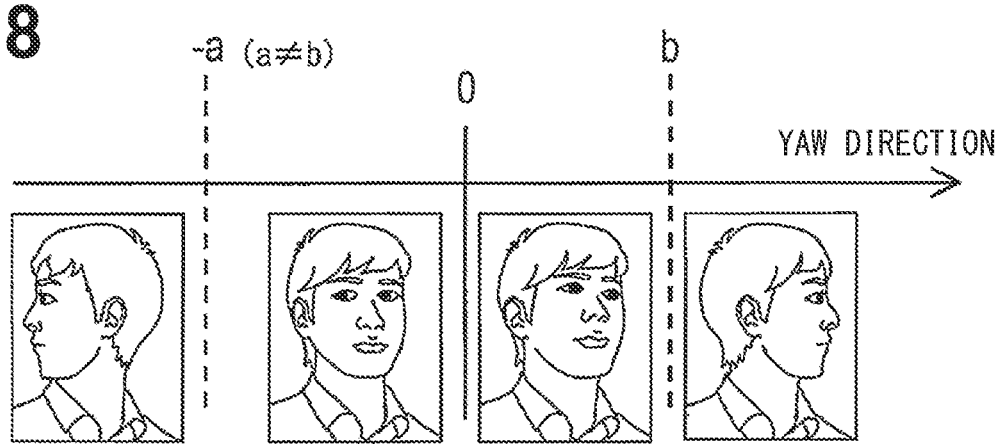
FIG. 8 is an explanatory diagram showing an example of predetermined areas used for face state summation.

As shown in FIG. 7, a feature quantity may include a result obtained by taking a predetermined angle range relative to the front direction based on the face states $\theta 1$ to $\theta 3$ as within range and the outside of the predetermined angle range as out of range and summing relevant frequencies with respect to each of within range and out of range. A predetermined angle range may be set as an identical angle on both sides of the front direction or may be set as different angles on both sides of the front direction, as shown in FIG. 8. Further, a feature quantity may include a mean value and a variance value of face orientation angles within range. Furthermore, when a face position is included in evaluation data, a feature quantity may include a frequency for each preset typical face position, a traveling speed measured when a face position changes, and the like.

Figure 9:
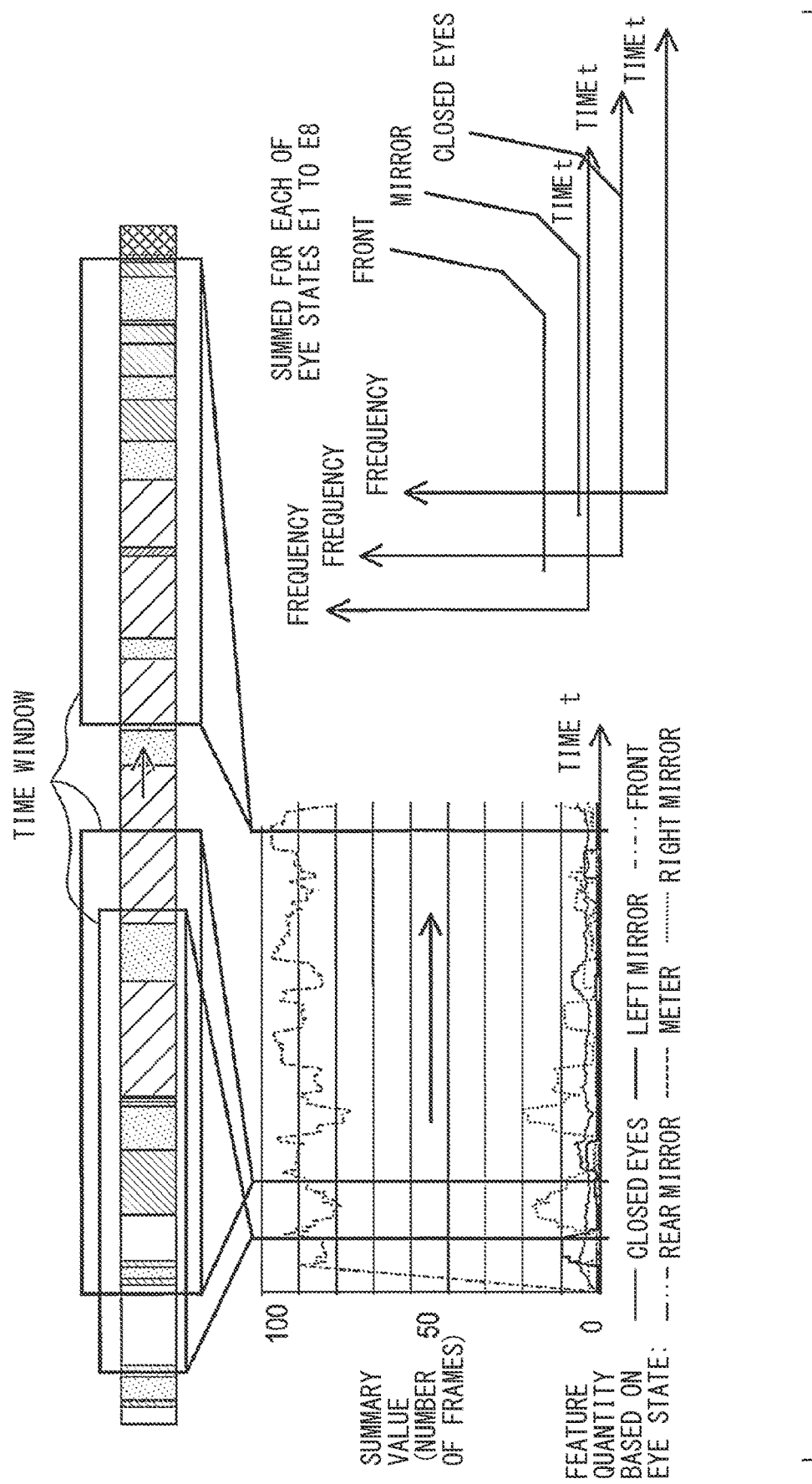
FIG. 9 is an explanatory diagram showing an example of feature quantities generated from the raw data of the gazing areas.

That is, each time an image frame is acquired, a plurality of feature quantities based on evaluation data with a range of a time window shifted by an amount equivalent to one frame are obtained. FIG. 9 expresses how a feature quantity obtained by summation with respect to the eye states E1 to E8 varies with a lapse of time in the form of graph.

At S70, subsequently, the processing unit 20 uses the feature quantity extracted at S60 to perform analysis processing to analyze the driver's condition and the like.

At S80, subsequently, the processing unit 20 presents an analysis result obtained at S70 to the driver via the HMI unit 30 and terminates the processing. To present an analysis result, an image may be used or voice may be used. S10 to S40 are equivalent to an information generation unit; S50 is equivalent to an acquisition unit; S60 is equivalent to an extraction unit; S70 is equivalent to an analysis unit; and S80 is equivalent to a display unit.

<1.3. Analysis and Presentation of Analysis Result>

A description will be given to concrete examples of the analysis processing at S70 and a method of presentation of an analysis result at S80.

<1.3.1. Example 1: Radar Chart>

Figure 10:
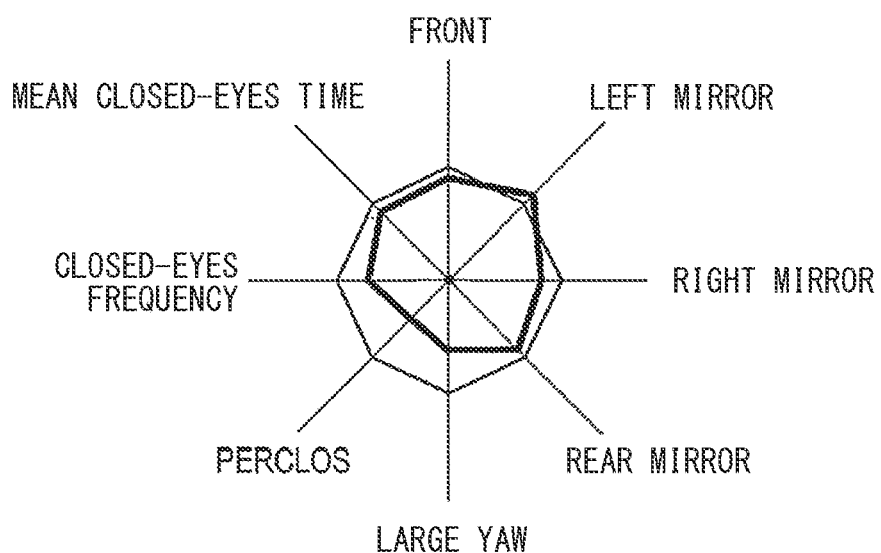
FIG. 10 is a radar chart used for presenting an analysis result.

A possible method for the analysis at S70 is, for example, that some of feature quantities considered to be related to a specific driver's condition are extracted and compared with statistical data prepared in advance. In this case, a possible method for the presentation of an analysis result at S80 is to display a radar chart as shown in FIG. 10.

Specifically, as a feature quantity to be extracted, for example, a summary value obtained when the gazing direction is the front E2, the left mirror E1, the right mirror E5, and the rear mirror E3 may be used. Further, as a feature quantity to be extracted, a summary value obtained when a face orientation is out of a predetermined range in the yaw direction $\theta 1$ (hereafter, referred to as large yaw) may be used. Furthermore, as a feature quantity to be extracted, PERCLOS, a closed-eyes time, a mean closed-eyes time, or the like as a feature quantity based on the closed-eyes E8 may be used.

Figure 11:
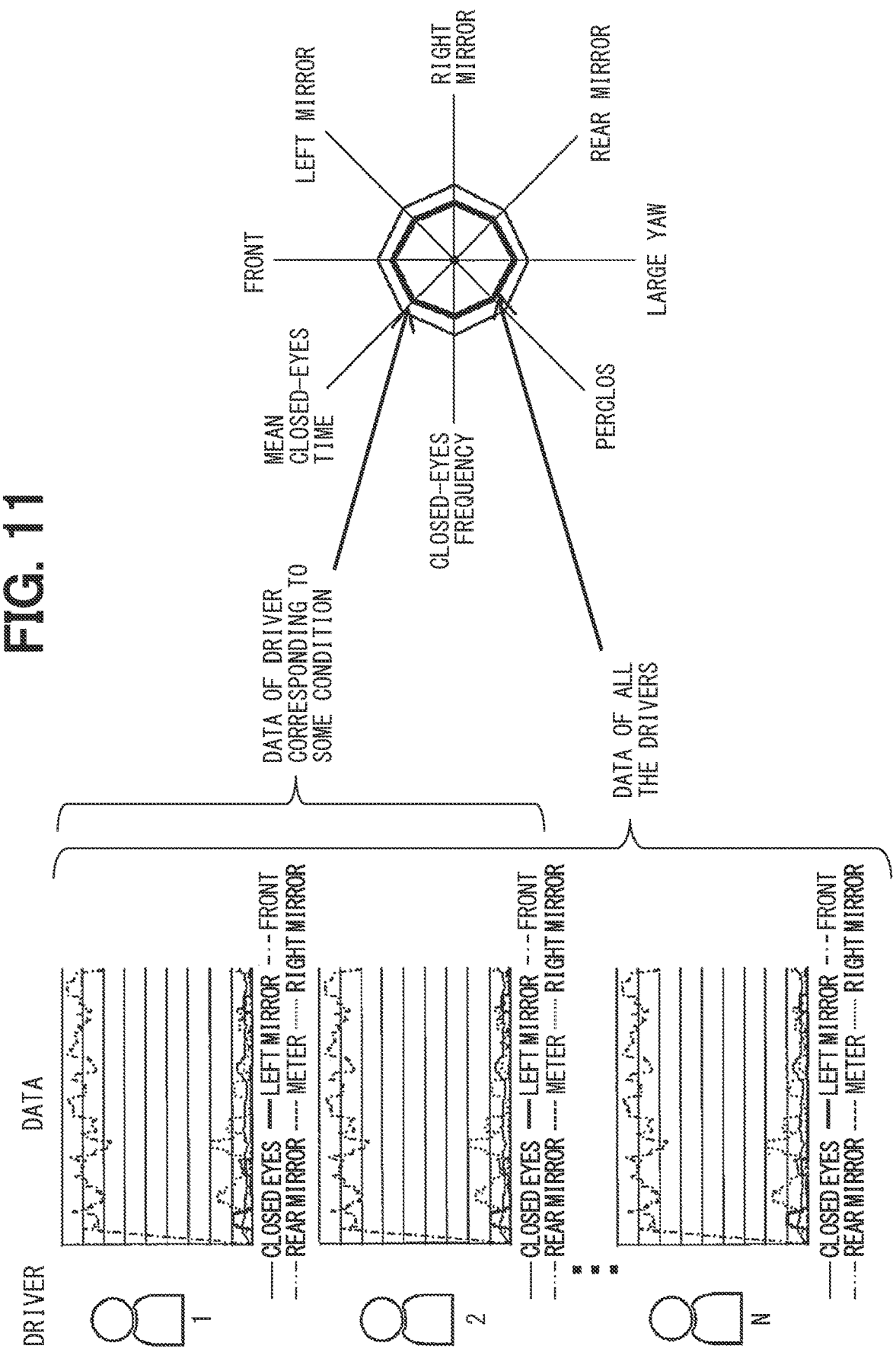
FIG. 11 is an explanatory diagram showing an example of a calculation method for statistical data indicated in a radar chart.

As statistical data to be compared with, as shown in FIG. 11, a mean value of data about all the drivers summed in advance may be used or a mean value of data about some drivers extracted under some condition may be used. Statistical data is equivalent to a reference value. As a condition used to extract a driver, gender, age, driving experience, or the like may be used. As a condition used to extract data regardless of drivers, region, time period, weather, or the like may be used.

Figure 12:
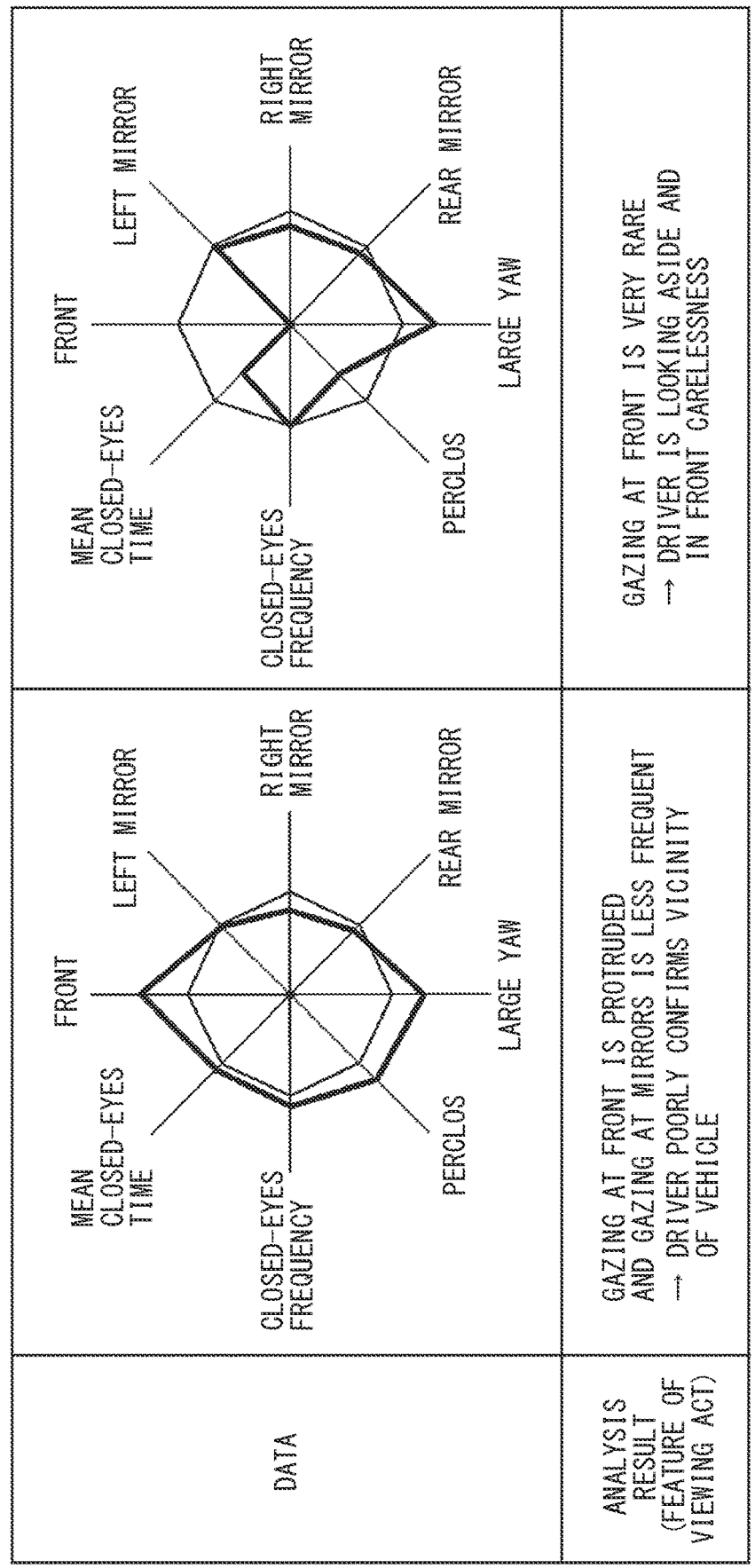
FIG. 12 is an explanatory diagram showing features of viewing acts read from radar charts.

For example, such an analysis result as shown in FIG. 12 can be obtained by confirming a display by a radar chart. In the left radar chart in FIG. 12, gazing at the front is protruded and gazing at mirrors is less frequent. From this tendency, a feature of the driver's viewing act that the driver poorly confirms the vicinity of the vehicle is understood. In the right radar chart in FIG. 12, the driver very rarely gazes at the front. From this tendency, a feature of the driver's viewing act that the driver is looking aside and is in a state of front carelessness is understood.

<1.3.2. Example 2: Analysis Using Function>

Figure 13:
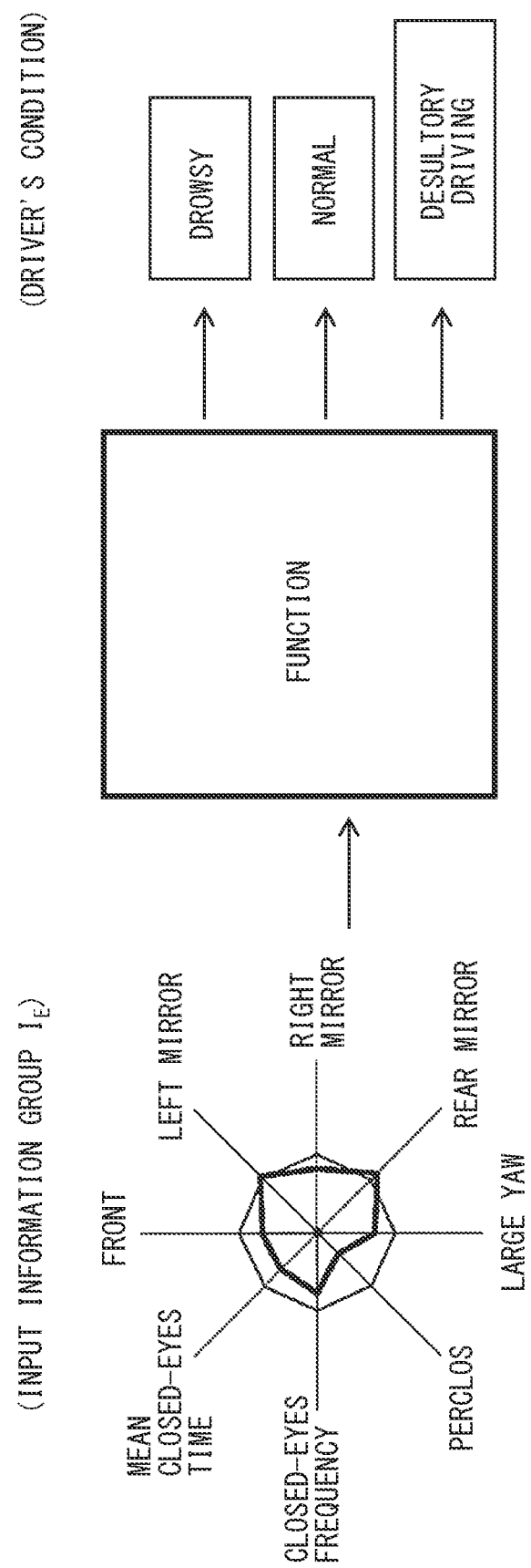
FIG. 13 is an explanatory diagram illustrating an analysis method utilizing a function.

In the analysis processing at S70, for example, as shown in FIG. 13, at least some of feature quantities generated at S60 may be taken as input information group $I_E$ and a function prepared in advance may be used to output a driver's tendency or a driver's condition as an analysis result. In the description here, a case where a regression function based on Gradient Boosting is used to output one of driver's conditions as an analysis result. That is, when a plurality of driver's conditions are analyzed, different regression functions are used for each of driver's conditions as analysis targets.

An input information group $I_E$ as input to the function may include the eight feature quantities used for a radar chart described above. The driver's conditions as output from the function may include "normal," "drowsy," and "desultory driving." When a driver's tendency is outputted, as shown in FIG. 12, "gazing at the front is frequent/less frequent," "gazing at mirrors is frequent/less frequent," or the like may be included.

<1.3.2.1. Overview>

As described above, an input information group $I_E$ is continuously extracted frame by frame using a so-called sliding window in which a time window is applied with a time equivalent to one frame of an image shifted. The analysis processing is performed on each of input information groups $I_E$ extracted frame by frame.

Here, the function outputs a score vector A as an analysis result. A score vector A includes an element that takes 1 when a driver's condition as an analysis target is applicable and an element that takes 1 when that is unapplicable. That is, the score vector A is a vector having two elements $a_1$, $a_2$ and is expressed by Expression (1). The score vector A takes a one-hot-format in which the value of any element is large and the value of the other element is small and ultimately gives a recognition result (that is, a driver's condition as an analysis target is applicable/unapplicable) based on an element having a larger value.

[Ex. 1]

$$A=[a_1 a_2]^T \tag{1}$$

In the analysis processing, as expressed by Expression (2), a score vector A representing an analysis result of a driver's condition is calculated by giving an initial value $A^{(0)}$ of score vector and correcting the score vector A with a correction amount R.

[Ex. 2]

$$A=A^{(0)}+R \tag{2}$$

As expressed by Expression (3), a correction amount R is obtained by causing an input information group $I_E$ cut out by a time window to act on a modified function $F_I$. The modified function $F_I$ is a function to which an additive model of a regression function using Gradient Boosting. Such a regression function is found in, for example, "One Millisecond Face Alignment with an Ensemble of Regression Trees", Vahid Kazemi and Josephine Sullivan, The IEEE Conference on CVPR, 2014, 1867-1874 (hereafter, referred to as Reference 1), "Greedy Function Approximation: A gradient boosting machine" Jerome H. Friedman, The Annals of Statistics Volume 29, Number 5 (2001), 1189-1232 (hereafter, referred to as Reference 2), and the like.

[Ex. 3]

$$R=F_I(I_E, A^{(0)}) \tag{3}$$

The modified function $F_I$ is a function whose value is regressively determined using I regression trees $RT_1$ to $RT_I$ prepared in advance and is defined by Expression (4), where I is an integer not less than 1. The regression trees $RT_1$ to $RT_I$ are a set of weak hypotheses having a tree structure. $F_0$ is an initial value of the modified function $F_I$ and $G_i$ is a regression function whose value is determined by the regression tree $RT_i$ identified by a regression tree index i, where i=1, 2, . . . , I. $\gamma$ is a learning rate and is set to $0<\gamma<1$. Over-learning is suppressed by reducing the value of $\gamma$.

[Ex. 4]

$$F_I(I_E, A^{(0)}) = F_0 + \gamma \sum_{i=1}^{I} G_i(I_E, A^{(0)}) \tag{4}$$

Figure 14:
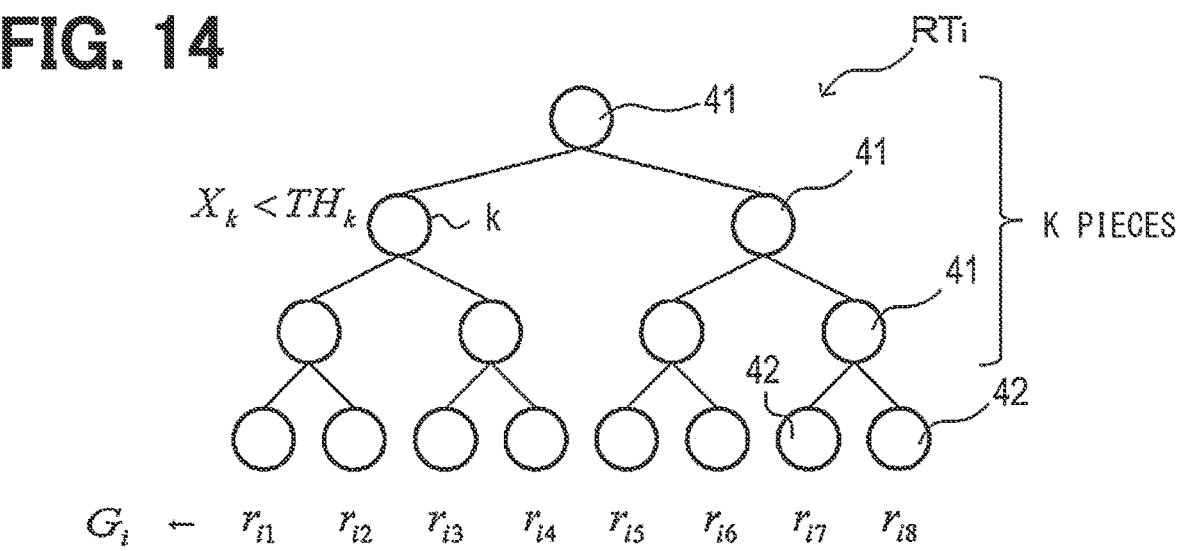
FIG. 14 is an explanatory diagram of a regression tree used for generating a regression function.

All of the I regression trees $RT_1$ to $RT_I$ have an identical structure. For example, as shown in FIG. 14, a binary tree in which nodes are sequentially branched into two is used for the regression tree $RT_i$. A node that provides a branch point of a branch of the regression tree $RT_i$ is referred to as ordinary node 41 and a node that provides a leaf of the regression tree $RT_i$ is referred to as terminal node 42. When k is taken as a node index identifying an ordinary node 41, comparative data $X_k$ and a threshold value $TH_k$ are correlated to the k-th ordinary node 41. The comparative data $X_k$ and the threshold value $TH_k$ are used for branch determination for determining to which low-order node the ordinary node 41 is branched. A concrete value $r_{i1} \sim r_{i8}$ of regression amount $G_i$ calculated by a regression tree $RT_i$ is correlated to each of the terminal nodes 42. K is taken as a number of ordinary nodes 41, except terminal nodes 42, among nodes forming the regression tree $RT_i$. K is an integer not less than 1.

For the comparative data $X_k$, any of M feature quantities $X_1$ to $X_M$ belonging to the input information group $I_E$ may be used. M is an integer not less than 1. Or, a result obtained by conducting some computation on a plurality of feature quantities selected from M feature quantities $X_1$ to $X_M$ may be used. However, when a result of computation on feature quantities is taken as comparative data $X_k$, as shown in FIG. 15, feature quantities identical in unit must be selected. For example, with respect to feature quantities for which a summary value for the eye states E1 to E8 is directly used, since any of the feature quantities is a count value, a result of computation between summary values for the eye states E1 to E8 can be taken as comparative data $X_k$. However, feature quantities representing PERCLOS, closed-eyes frequency, and mean closed-eyes time represent a time or a ratio; therefore, a result of computation between these feature quantities and feature quantities directly using a summary value cannot be taken as comparative data $X_k$.

The description will be back to FIG. 14. At each ordinary node 41 identified by a node index k of a regression tree $RT_i$, which branch reaching to an ordinary node 41 or a terminal node 42 in the next hierarchy should be selected is determined according to whether the comparative data $X_k$ is smaller than the threshold value $TH_k$. That is, the processing arrives at any of a plurality of terminal nodes 42 by repeating the processing of sequentially selecting a branch of the regression tree $RT_i$ according to a result of comparison at each ordinary node 41. Any of regression amounts $r_{i1}$, $r_{i2}$, $r_{i3}$, . . . correlated to the terminal node 42 at which the processing arrived becomes a value of the regression function $G_i$ and by extension, becomes a part of a value of the modified function $F_I$.

In the analysis processing, as mentioned above, an initial value $A^{(0)}$ of a score vector A, an initial value $F_0$ of a modified function $F_I$, and parameters defining a regression tree $RT_i$ (that is, comparative data $X_1$ to $X_K$, threshold values $TH_1$ to $TH_K$, regression amounts $r_{i1}$, $r_{i2}$, $r_{i3}$, . . . ) must be prepared in advance. In the following description, $A^{(0)}$, $F_0$, $X_1$ to $X_K$, $TH_1$ to $TH_K$, $r_{i1}$, $r_{i2}$, $r_{i3}$, . . . are collectively referred to as analysis parameters.

The analysis parameters are generated by the learning part 22 of the processing unit 20 performing learning processing. However, learning processing need not necessarily be performed by the processing unit 20 and may be performed by any other device than the processing unit 20.

<1.3.2.2. Learning>

Figure 16:
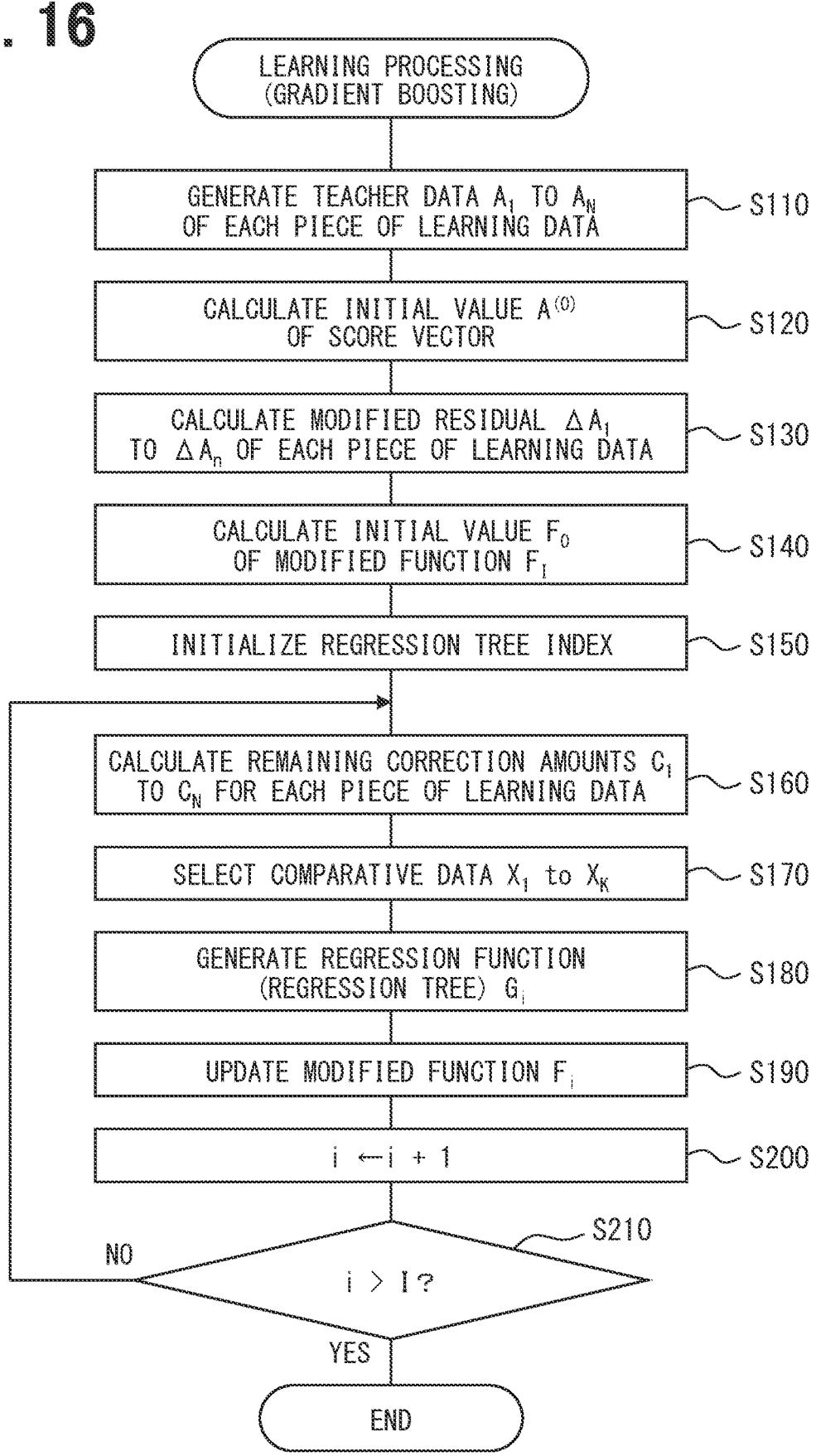
FIG. 16 is a flowchart of learning processing for generating a regression tree by Gradient Boosting.
Figure 17:
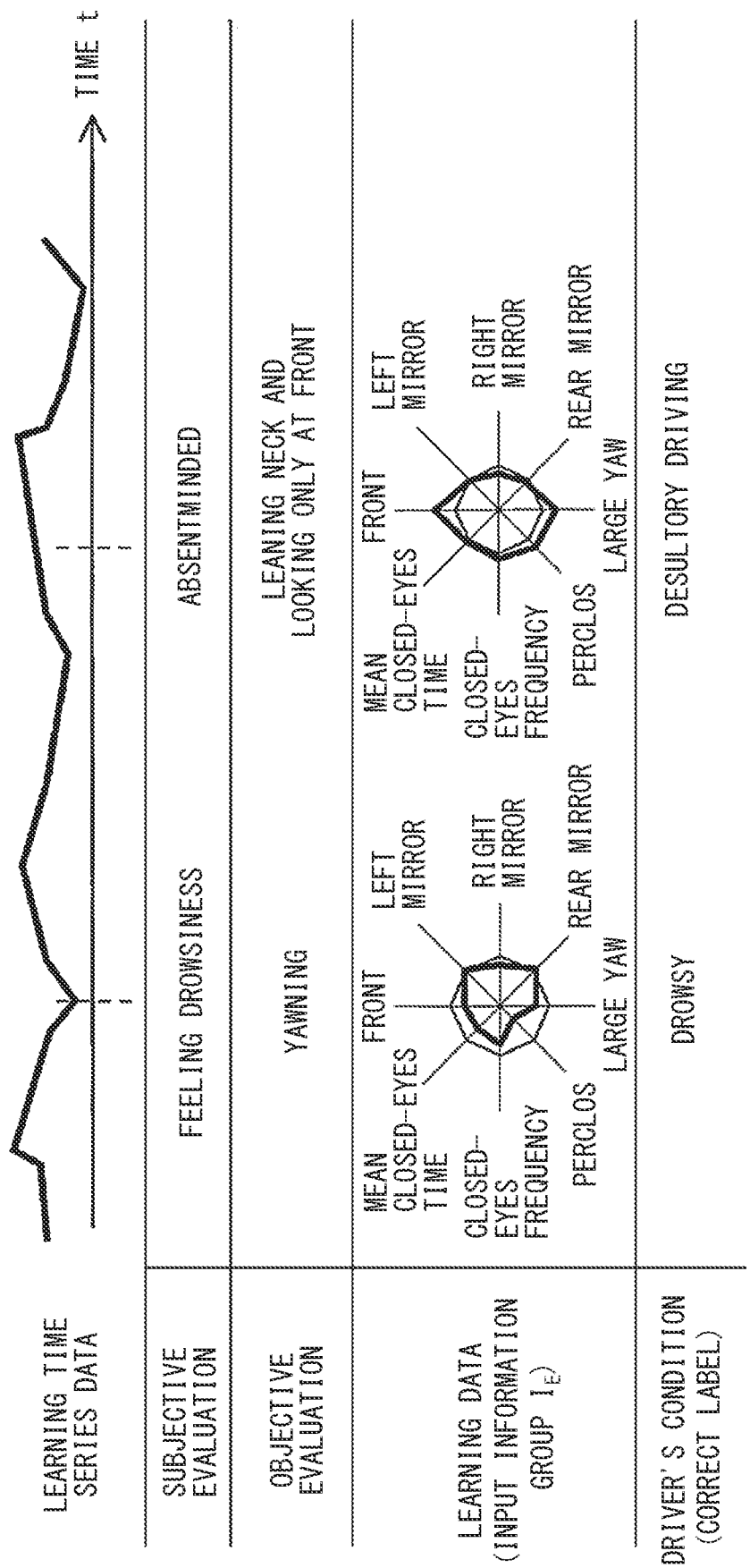
FIG. 17 is an explanatory diagram showing a relation between learning data and correct labels used for teacher data.

A description will be given to learning processing for setting analysis parameters with reference to the flowchart in FIG. 16. When learning processing is performed, time series data of the eye states E1 to E8 and face states θ1 to θ3 prepared for learning (hereafter, referred to as learning time series data) is stored in the memory 20b. The learning time series data is data obtained by an indefinite number of drivers driving in various situations. Learning time series data is previously given a correct label of a driver's condition frame by frame. A correct label is generated by collecting subjective evaluation and objective evaluation of a driver's condition in parallel with collection of learning time series data and estimating the driver's condition from the subjective evaluation and the objective evaluation as shown in FIG. 17, for example. Examples of subjective evaluation are "feeling drowsiness," "absentminded," and the like and examples of objective evaluation are "yawning," "leaning neck," "looking only at the front," and the like.

At S110, the processing unit 20 takes, as learning data, each of N input information groups $I_E$ cut out from learning time series data stored in the memory 20b using a time window and generates a correct answer value (hereafter, referred to as teacher data) $A_1$ to $A_N$ of a score vector A for each piece of the learning data. N is an integer not less than 1.

Specifically, the correct label given for each frame of an image included in the learning data is referred to, to generate teacher data $A_1$ to $A_N$. When n=1, 2, . . . , N, a correct label is given to a frame of each image included in n-th piece of the learning data. When the driver's condition as an analysis target is applicable based on this correct label, $A_n$=(1,0) is set and when the driver's condition is unapplicable, $A_n$=(0,1) is set.

At S120, subsequently, the processing unit 20 calculates an initial value $A^{(0)}$ of the score vector. For the initial value $A^{(0)}$ of the score vector, for example, a mean value of the teacher data $A_1$ to $A_N$ generated at S110 may be used.

At S130, subsequently, the processing unit 20 calculates a modified residual $\Delta A_n$, which is a difference between teacher data $A_n$ and the initial value $A^{(0)}$ of the score vector, with respect to each of N pieces of learning data according to Expression (5).

[Ex. 5]

$$\Delta A_n = A_n - A^{(0)} \quad (5)$$

At S140, subsequently, the processing unit 20 uses Expression (6) to calculate an initial value $F_0$ of a modified function $F_I$ used for calculation of a correction amount R.

[Ex. 6]

$$F_0 = \underset{V}{\operatorname{argmin}} \sum_{n=1}^{N} \|\Delta A_n - V\|^2 \quad (6)$$

Expression (6) means that when a distance between a modified residual $\Delta A_n$ in each piece of learning data and any vector V having the same dimension as the score vector A does is totalized with respect to all the pieces of learning data, a vector V minimizing the total value is taken as an initial value $F_0$ of the modified function $F_I$.

At S150, subsequently, the processing unit 20 initializes a regression tree index i used for identification of regression trees $RT_1$ to $RT_I$ to 1.

At S160, subsequently, the processing unit 20 uses Expression (7) to calculate remaining correction amounts $c_1$ to $c_N$ for each piece of learning data.

[Ex. 7]

$$c_i = \Delta A_n - F_{i-1}(I_E, A^{(0)}) \quad (7)$$

At S170, subsequently, the processing unit 20 generates a regression tree $RT_i$ by using the learning data to sequentially set comparative data $X_1$ to $X_K$ and threshold values $TH_1$ to $TH_K$ used at each ordinary node 41 of the regression tree $RT_i$. To generate a regression tree $RT_i$, for example, a method described in Section 2.3.2 of Reference 1 may be used. Especially, to select comparative data $X_1$ to $X_K$, comparative data may be selected at random from among all the selectable comparative data candidates or an optimum one may be searched for based on a round-robin system.

That comparative data $X_1$ to $X_K$ is selected by such learning means that comparative data correlated to a feature high in contribution rate in analysis of a driver's condition is automatically selected from among all the selectable comparative data candidates.

At S180, subsequently, the processing unit 20 generates a regression tree $RT_i$ by: taking the comparative data $X_1$ to $X_K$ selected at S170 as an index for classifying learning data; and setting such threshold values $TH_1$ to $TH_K$ that a value close to remaining correction amounts $c_1$ to $c_N$ in all the pieces of learning data can be obtained. That is, a regression function $G_i$ implemented by the regression tree $RT_i$ is generated.

At S190, subsequently, the processing unit 20 uses the regression function $G_i$ generated at S180 to update the modified function $F_i$ by Expression (8).

[Ex. 8]

$$F_i(I_E, A^{(0)}) = F_{i-1}(I_E, A^{(0)}) + \gamma \cdot G_i(I_E, A^{(0)}) \quad (8)$$

At S200, subsequently, the processing unit 20 increments the regression tree index i by 1.

At S210, subsequently, the processing unit 20 determines whether i>I. When a negative judgment is made at S210, the processing is returned to S160 to generate a new regression tree $RT_i$. When an affirmative judgment is made at S210, the processing is terminated.

In the learning processing, I regression functions $G_1$ to $G_I$ (that is, I regression trees $RT_1$ to $RT_I$) are generated for one modified function $F_j$.

<1.3.2.3. Analysis Processing>

Figure 18:
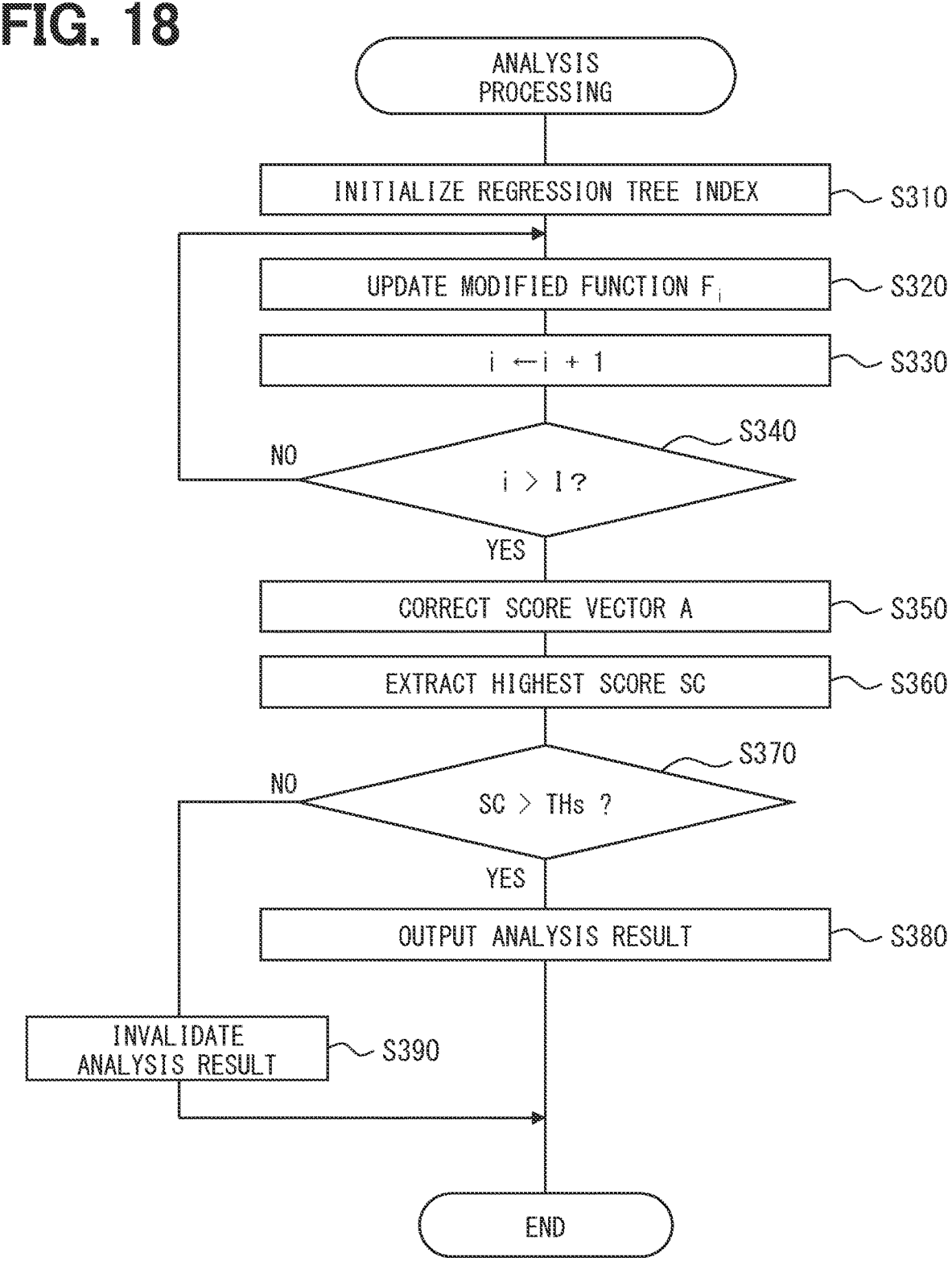
FIG. 18 is a flowchart of analysis processing using a regression function generated by Gradient Boosting.

A description will be given to the analysis processing performed by the processing unit 20 at S70 with reference to the flowchart in FIG. 18. In the analysis processing, the analysis parameters generated through the above-mentioned learning processing are used. The analysis processing may be performed each time an image is acquired at S10, that is, frame by frame or may be performed for each plurality of frames.

At S310, first, the processing unit 20 initializes the regression tree index i to 1.

At S320, subsequently, the processing unit 20 uses a regression tree $RT_i$ identified by the regression tree index i, the input information group $I_E$ acquired at S60, and determination parameters of the regression tree $RT_i$ calculated through the learning processing to acquire a value of the regression function $G_i$ and uses Expression (8) to update the modified function $F_i$.

At S330, subsequently, the processing unit 20 increases the regression tree index i by 1.

At S340, subsequently, the processing unit 20 determines whether i>I. That is, it is determined whether all of the I regression trees $RT_1$ to $RT_I$ have been used for calculation of the modified function $F_i$. When a negative judgment is made at S340, the processing unit 20 returns the processing to S320 and when an affirmative judgment is made at S340, the processing unit causes the processing to proceed to S350. By the processing of S320 to S340, the modified function $F_I$ indicated by Expression (4) is ultimately calculated and as indicated by Expression (3), a value obtained by this modified function $F_i$ provides a correction amount R for the initial value $A^{(o)}$ of the score vector.

At S350, the processing unit 20 generates a score vector A corrected using Expression (2).

At S360, subsequently, the processing unit 20 extracts an element having a larger value (hereafter, referred to as highest score SC) among the corrected score vector A.

At S370, the processing unit 20 determines whether the extracted highest score SC is higher than a preset threshold value $TH_s$. $TH_s$ is a threshold value for determining the reliability of an analysis result. When $SC>TH_s$, the processing unit 20 causes the processing to proceed to S380 and when $SC \leq TH_s$, the processing unit causes the processing to proceed to S390.

At S380, the processing unit 20 outputs an analysis result correlated to an element having the highest score SC, that is, whether a driver's condition as an analysis target is applicable or unapplicable and terminates the processing.

At S390, the processing unit 20 considers the analysis result indicated by the score vector A to be low in reliability, invalidates the analysis result, and terminates the processing.

<1.4. Effects>

According to the embodiment described in detail up to this point, the following effects are brought about;

(1a) According to the present embodiment, a feature quantity extracted from the eye states E1 to E8 and the face states θ1 to θ3 is used to analyze whether a driver's condition as an analysis target is applicable and an analysis result is presented to the driver. That is, unlike the relevant technologies, an analysis is made without paying special attention to the front direction. Therefore, a state in which a driver is intentionally viewing any other direction than the front direction can be precisely determined and misidentification as inattentiveness or the like can be suppressed.

(1b) According to the present embodiment, a radar chart is used as a method for presenting an analysis result and statistical data of a mean value of an indefinite number of drivers and the like is presented together with a feature quantity extracted about a driver him/herself. For this reason, the driver is allowed to easily compare the driver him/herself with others. As a result, the driver can be made to easily understand the driver's own tendency and features during driving.

(1c) According to the present embodiment, at least some of feature quantities are taken as an input information group $I_E$, a regression function generated by Gradient Boosting is used to estimate whether a driver's condition as an analysis target is applicable, and a result of estimation is outputted as an analysis result. For this reason, a regression function can be generated without technical knowledge about a relation between a driver's condition and a feature quantity and a highly accurate analysis can be made.

(1d) According to the present embodiment, not only information about gazing direction but also information about closed-eyes state is use for analysis.

Therefore, the accuracy of analysis about a driver's condition such as health deterioration and inattentiveness can be enhanced.

<2. Second Embodiment>
<2.1. Difference from First Embodiment>

Since the basic configuration of the second embodiment is identical with that of the first embodiment, a description will be given to a difference between them. The same reference numerals as in the first embodiment indicate identical configuration elements and a preceding description will be referred to.

In the first embodiment, Gradient Boosting is used to generate a regression function (that is, regression tree) used for analysis. The second embodiment is different from the first embodiment in that a Random forest is used to generate a regression function.

<2.2. Learning Processing>

Figure 19:
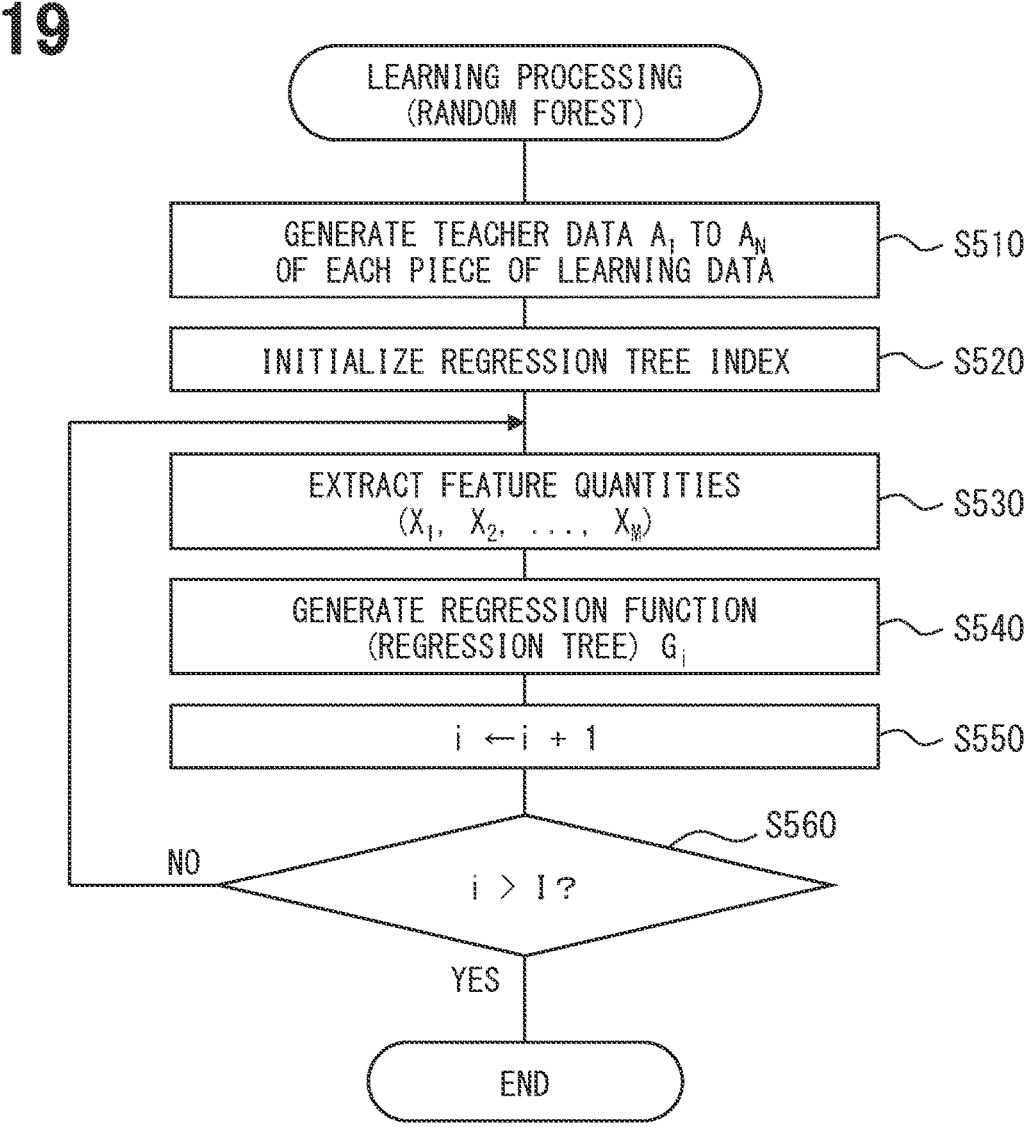
FIG. 19 is a flowchart of learning processing for generating a regression tree by a Random forest in a second embodiment.

A description will be given to learning processing for the processing unit 20 in the second embodiment to implement the functions of the learning part 22 with reference to the flowchart in FIG. 19. This learning processing is performed in place of the learning processing in the first embodiment described with reference to FIG. 16.

When learning processing is performed, as in the first embodiment, learning status information is stored in the memory 20b. Learning status information is given a correct label of a driver's condition frame by frame in advance. In the present example, as a correct label of a driver's condition, a state in which a driver is not feeling drowsy (hereafter, referred to as sound) is taken as 0 and a state in which a driver is feeling drowsy (hereafter, referred to as drowsy) is taken as 1.

At S510, as in the processing at S310, the processing unit 20 takes, as learning data, N input information groups $I_E$ cut out using a time window and generates teacher data $A_1$ to $A_N$ as correct answer value for each piece of the learning data. Teacher data takes a value of 0 or 1.

At S520, subsequently, the processing unit 20 initializes the regression tree index i to 1.

At S530, subsequently, the processing unit 20 extracts M feature quantities $X_1$ to $X_M$ from each piece of the learning data. The M feature quantities are extracted from more than M feature quantity candidates for each regression tree index i in different combination patterns.

At S540, subsequently, the processing unit 20 uses the feature quantities $X_1$ to $X_M$ extracted at S530 as an index for classifying learning data at each node in a regression tree $RT_i$ to generate the regression tree $RT_i$.

Specifically, each piece of learning data assigned to an ordinary node 41 of interest is distributed to two lower-order nodes depending on whether the feature quantity $X_m$ is larger than a threshold value $a_m$. The regression tree $RT_i$ is generated by: using the learning data distributed at this time to calculate an error $Q_m$ for each lower-order node; and selecting a threshold value $a_m$ so as to minimize this error $Q_m$. That is, a regression function $G_i$ implemented by the regression tree $RT_i$ is generated.

When the regression tree $RT_i$ is generated, all the pieces of learning data are assigned to the node $N_1$ positioned at the top of the regression tree $RT_i$. The error $Q_m$ is calculated as described below: an assigned value of 0 indicating "normal" is assigned to a first node of the two lower-order nodes and an assigned value of 1 indicating "drowsy" is assigned to a second node; and a square error of teacher data of learning data assigned to each node and the assigned value of the node is taken as the error $Q_m$.

At S550, subsequently, the processing unit 20 increases the regression tree index i by 1.

At S560, subsequently, the processing unit 20 determines whether the regression tree index i is larger than the total number I of the regression trees $RT_i$ used for generation of a regression function. When i>I, the processing unit 20 terminates the processing and when the processing unit returns the processing to S530 and restarts the processing from selection of M feature quantities to generate a new regression tree.

I regression trees $RT_1$ to $RT_I$ are generated by the learning processing. Specifically, comparative data $X_{ik}$ and a threshold value $a_{ik}$ set for each ordinary node 41 constituting the regression tree $RT_i$ and an output value set for each terminal node 42 are generated as analysis parameters. k is an index for identifying each node constituting the regression tree $RT_i$.

<2.3. Analysis Processing>

Figure 20:
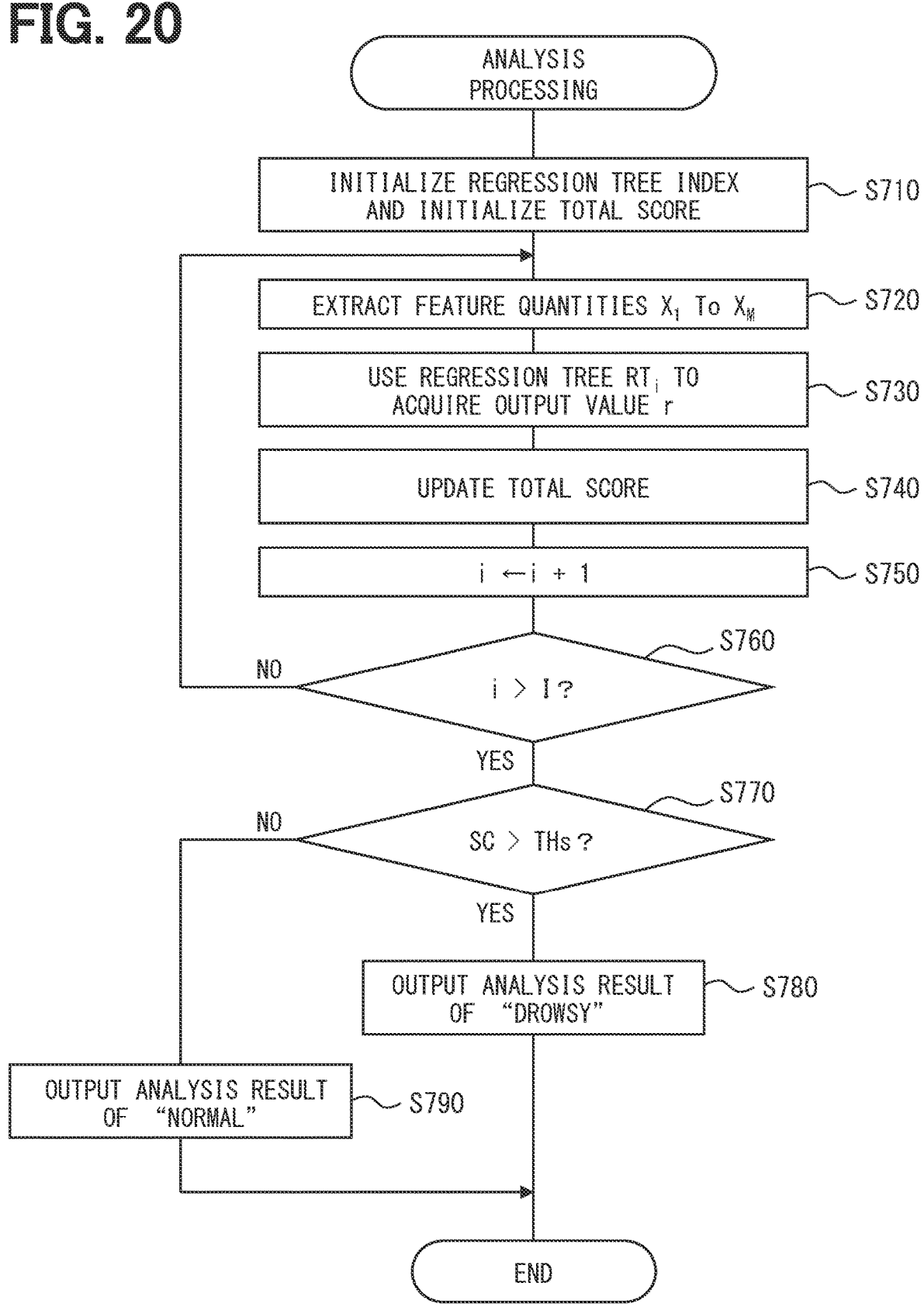
FIG. 20 is a flowchart of analysis processing using a regression function generated by a Random forest.

A description will be given to analysis processing for the processing unit 20 in the second embodiment to implement the functions of the driving analysis part 21 with reference to the flowchart in FIG. 20. This analysis processing is performed in place of the analysis processing in the first embodiment described with reference to FIG. 18. In the analysis processing in the second embodiment, the analysis parameters generated by the above-mentioned learning processing are used.

At S710, the processing unit 20 initializes the regression tree index i to 1 and further initializes the total score SC to 0.

At S720, subsequently, the processing unit 20 extracts feature quantities $X_1$ to $X_M$ used as comparative data in the regression tree $RT_i$ from the input information group $I_E$.

At S730, subsequently, the processing unit 20 acquires an output value r by using the feature quantities $X_1$ to $X_M$ extracted at S720 to sequentially follow the regression tree $RT_i$.

At S740, subsequently, the processing unit 20 updates the total score SC by adding the output value r to the total score SC.

At S750, subsequently, the processing unit 20 increases the regression tree index i by 1.

At S760, subsequently, the processing unit 20 determines whether the regression tree index i is larger than the total number I of the regression trees $RT_i$ used for generating a regression function. When i>I, the processing unit 20 causes the processing to proceed to S770 and when i≤I, the processing unit 20 returns the processing to S720.

At S770, subsequently, the processing unit 20 determines whether the total score SC is higher than a preset threshold value $TH_s$. When SC>$TH_s$, the processing unit 20 causes the processing to proceed to S780 and when SC≤$TH_s$, the processing unit 20 causes the processing to proceed to S790.

At S780, the processing unit 20 outputs a driver's condition as an analysis target, that is, an analysis result to the effect that the driver's condition corresponds to "drowsy" and terminates the processing.

At S790, the processing unit 20 outputs an analysis result to the effect that a driver's condition as an analysis target is unapplicable and the driver's condition corresponds to "sound" and terminates the processing.

<2.4. Effects>

According to the second embodiment described in detail up to this point, the same effects as the above-mentioned effects (1a) to (1d) of the first embodiment are brought about.

<3. Other Embodiments>

Up to this point, a description has been given to embodiments of the present disclosure but the present disclosure is not limited to the above-mentioned embodiments and can be variously modified and implemented.

Figure 21:
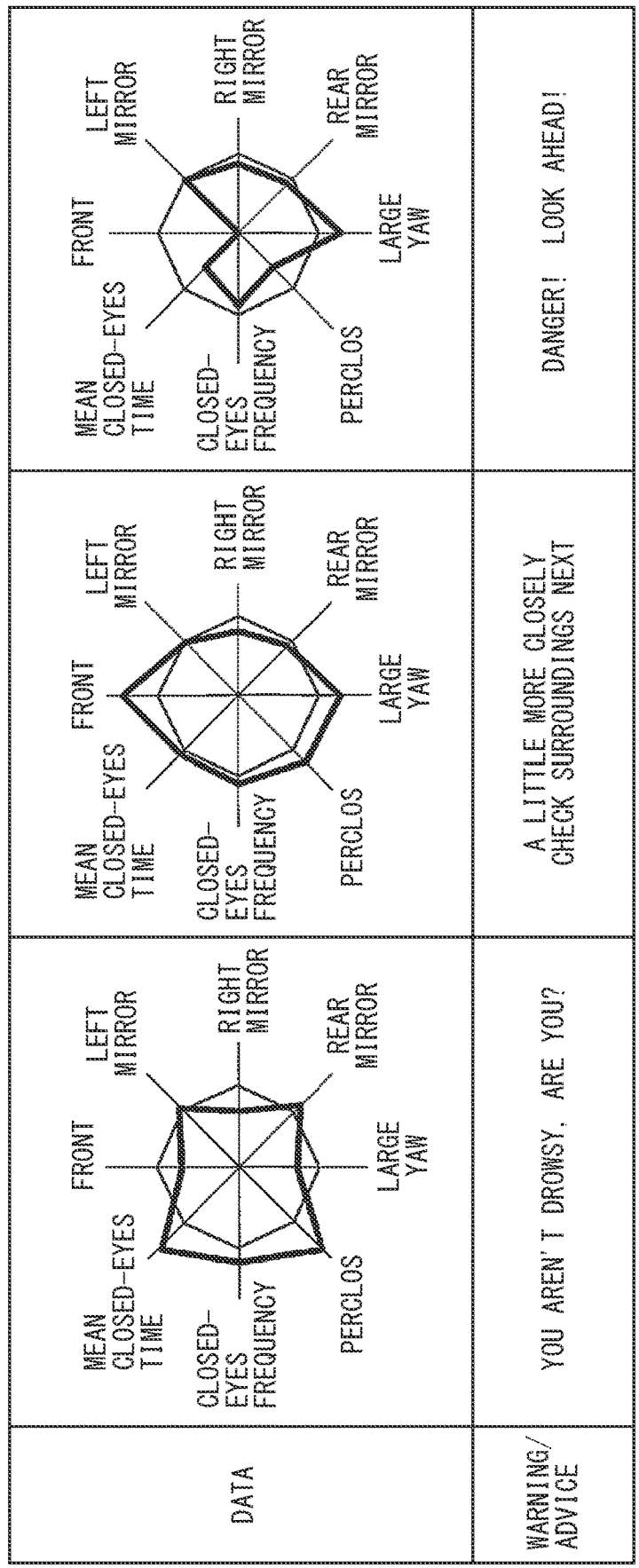
FIG. 21 is an explanatory diagram showing an example of concrete contents of a warning or advice in cases where the warning or advice is presented to a driver as an analysis result.

(3a) According to the above-mentioned embodiments, a driver's condition as an analysis result is presented to the driver but what is presented to a driver is not limited to the driver's condition. As shown in FIG. 21, for example, a warning or an advice suitable for a driver's condition may be presented to the driver. For presentation, not only an image but also a voice may be used.

Figure 22:
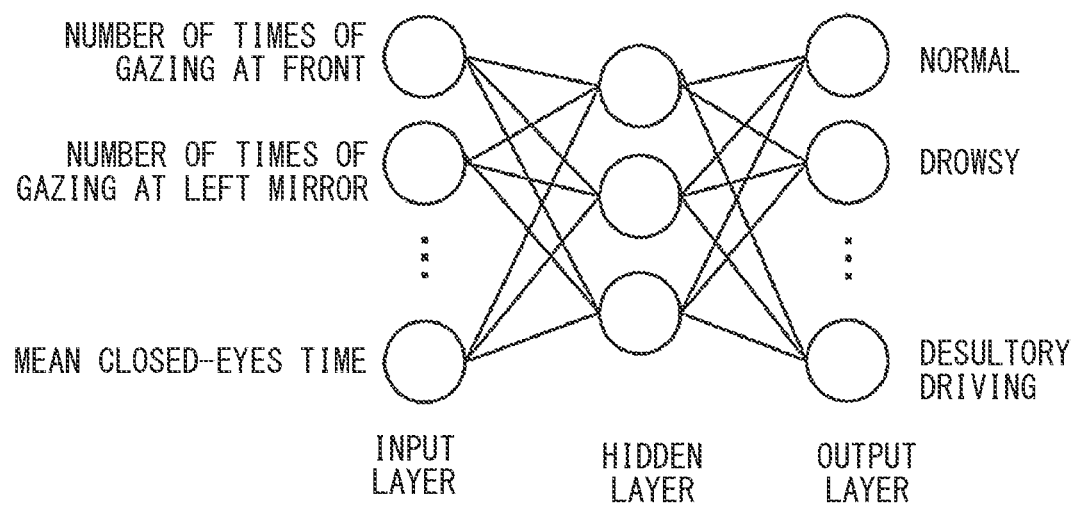
FIG. 22 is an explanatory diagram illustrating a case where a neural network is used as a function used for analyses.

(3b) According to the above-mentioned embodiments, a regression tree is used to generate a function used for analysis processing. Instead of a regression tree, for example, a support vector machine, such a neural network as shown in FIG. 22, or the like may be used.

(3c) According to the above-mentioned embodiments, an analysis result by analysis processing is presented to a driver via the HMI unit 30 but usage of an analysis result is not limited to presentation to a driver. For example, an analysis result may be used in vehicle control for driving assistance or the like.

(3d) According to the above-mentioned embodiments, the eye states E1 to E8 extracted from a driver's face image and a feature quantity extracted from the face states θ1 to θ3 are used in analysis processing but information used in analysis processing is not limited to the feature quantity. For example, in addition to the feature quantity, a feature quantity extracted from information representing a driver's driving operation, information representing a behavior of a vehicle, information representing a surrounding situation of a vehicle, or the like may be used in analysis processing.

(3e) The processing unit 20 described in the present disclosure and a technique therefor may be implemented by a dedicated computer provided by configuring a processor and a memory programmed to execute one or more functions crystallized by a computer program. Or, the processing unit 20 described in the present disclosure and a technique therefor may be implemented by a dedicated computer provided by configuring a processor with one or more dedicated hardware logic circuits. Alternatively, the processing unit 20 described in the present disclosure and a technique therefor may be implemented by one or more dedicated computers configured with a combination of a processor and a memory programmed to execute one or more functions and a processor configured with one or more hardware logic circuits. A computer program may be stored in a computer-readable non-transitory tangible recording medium as an instruction to be executed by a computer. A technique for executing the functions of each part included in the processing unit 20 need not necessarily include software and all of the functions may be implemented using one or more pieces of hardware.

(3f) A plurality of functions provided in one component in the above-mentioned embodiments may be implemented by a plurality of components or one function provided in one component may be implemented by a plurality of components. A plurality of functions provided in a plurality of components may be implemented by one component or one function implemented by a plurality of components may be implemented by one component. Some of the configuration elements of the above-mentioned embodiments may be omitted. At least some of the configuration elements of the above-mentioned embodiments may be added to or replaced with others of the configuration elements of the above-mentioned embodiments.

(3g) Aside from the above-mentioned driving analysis device 1, the present disclosure may be implemented in various modes, including a system including the driving analysis device 1 as a component, a program for causing a computer to function as the processing unit 20 constituting the driving analysis device 1, a non-transitory tangible recording medium, such as semiconductor memory, with the program recorded thereon, a driving analysis method, and the like.

What is claimed is:

1. A driving analysis device comprising:
an information generation unit configured to generate a time series of detection elements including a line-of-sight direction indicating to which of a plurality of preset viewable areas a line of sight of a driver driving a vehicle is oriented and an open/closed state of driver's eyes;
an acquisition unit configured to acquire evaluation data from the time series of the detection elements using a time window having a preset time width;
an extraction unit configured to extract a plurality of feature quantities including at least a result of summation of appearance frequencies with respect to each of the detection elements from the evaluation data;
an analysis unit configured to analyze a driver's tendency using a function receiving, as input, at least a part of the feature quantities extracted by the extraction unit; and
a display configured to display the at least the part of the feature quantities extracted by the extraction unit in a form of radar chart.

2. The driving analysis device according to claim 1, wherein
the display is configured to use, as a reference value shown in the radar chart, either a mean value of the feature quantities about an indefinite number of drivers or a mean value of the feature quantities about the driver as an analysis target of the driving analysis device acquired in past.

3. The driving analysis device according to claim 1, wherein
the feature quantities extracted by the extraction unit include a value indicating a feature of state transition within an identical detection element or between the plurality of the detection elements.

4. The driving analysis device according to claim 1, wherein
the analysis unit is configured to use either a support vector machine or a neural network as the function.

5. A driving analysis device comprising:
an information generation unit configured to generate a time series of detection elements including a line-of-sight direction indicating to which of a plurality of preset viewable areas a line of sight of a driver driving a vehicle is oriented and an open/closed state of driver's eyes;
an acquisition unit configured to acquire evaluation data from the time series of the detection elements using a time window having a preset time width;
an extraction unit configured to extract a plurality of feature quantities including at least a result of summation of appearance frequencies with respect to each of the detection elements from the evaluation data; and
an analysis unit configured to analyze a driver's tendency using a function receiving, as input, at least a part of the feature quantities extracted by the extraction unit, wherein
the analysis unit is configured to use, as the function, a regression function obtained using either a Random forest or Gradient Boosting.

6. The driving analysis device according to claim 5, wherein the analysis unit is configured to use at least a result of computation on two or more target feature quantities selected from the feature quantities as comparative data used for branch determination at each node in a regression tree used for generating the regression function, and
wherein, for the target feature quantities, the feature quantities that are identical in unit of value are selected.

7. A driving analysis method comprising:
generating a time series of detection elements, the detection elements including a line-of-sight direction indicating to which of a plurality of preset viewable areas a line of sight of a driver driving a vehicle is oriented and an open/closed state of driver's eyes;
acquiring evaluation data from the time series of the detection elements using a time window having a preset time width;
extracting a plurality of feature quantities including at least a result of summation of appearance frequencies with respect to each of the detection elements from the evaluation data;
analyzing a driver's tendency by using a function receiving, as input, at least a part of the feature quantities extracted; and
displaying the at least the part of the feature quantities extracted in a form of radar chart.

8. A driving analysis device comprising:
a processor and a memory configured to:
generate a time series of detection elements including a line-of-sight direction indicating to which of a plurality of preset viewable areas a line of sight of a driver driving a vehicle is oriented and an open/closed state of driver's eyes;
acquire evaluation data from the time series of the detection elements using a time window having a preset time width;

extract a plurality of feature quantities including at least a result of summation of appearance frequencies with respect to each of the detection elements from the evaluation data;

analyze a driver's tendency using a function receiving, as input, at least a part of the feature quantities extracted; and display the at least the part of the feature quantities extracted in a form of radar chart.

* * * * *